United States Patent
Bonner et al.

(10) Patent No.: US 6,918,908 B2
(45) Date of Patent: Jul. 19, 2005

(54) METHODS AND APPARATUS FOR ACCESSING AND STABILIZING AN AREA OF THE HEART

(75) Inventors: Matthew D. Bonner, Plymouth, MN (US); Raymond W. Usher, Coon Rapids, MN (US); Victor T. Chen, Minneapolis, MN (US); James R. Keogh, Maplewood, MN (US)

(73) Assignee: Medtronic, Inc., Minneapolis, MN (US)

( * ) Notice: Subject to any disclaimer, the term of this patent is extended or adjusted under 35 U.S.C. 154(b) by 178 days.

(21) Appl. No.: 10/622,147

(22) Filed: Jul. 17, 2003

(65) Prior Publication Data

US 2004/0138527 A1 Jul. 15, 2004

Related U.S. Application Data

(63) Continuation-in-part of application No. 10/342,932, filed on Jan. 15, 2003, now Pat. No. 6,837,848.

(51) Int. Cl.[7] ............................................. A61B 18/18
(52) U.S. Cl. ..................... 606/41; 604/115; 600/114; 600/37; 606/1
(58) Field of Search ................. 604/115, 117, 604/93.01, 164.4, 506, 500, 176, 902, 264, 35, 96.01, 528, 908; 606/205, 167, 1, 108, 41; 600/508, 374, 115, 201, 509, 114, 204, 205, 37, 210

(56) References Cited

U.S. PATENT DOCUMENTS

| | | | |
|---|---|---|---|
| 3,902,501 A | 9/1975 | Citron et al. ............... 128/418 |
| 4,662,376 A | * 5/1987 | Belanger .................... 606/125 |
| 4,723,940 A | * 2/1988 | Wiegerinck ................. 604/115 |
| 4,815,478 A | 3/1989 | Buchbinder et al. ......... 128/772 |
| 4,898,577 A | 2/1990 | Badger et al. ................ 604/53 |
| 4,940,062 A | 7/1990 | Hampton et al. ........... 128/772 |
| 4,991,578 A | 2/1991 | Cohen .................... 128/419 D |
| 5,071,428 A | 12/1991 | Chin et al. ................. 606/184 |
| 5,076,285 A | 12/1991 | Hess et al. ................. 128/186 |
| 5,336,252 A | 8/1994 | Cohen ........................ 607/119 |
| 5,452,733 A | 9/1995 | Sterman et al. ............ 128/898 |
| 5,464,447 A | 11/1995 | Fogarty et al. ............. 607/129 |
| 5,545,200 A | 8/1996 | West et al. ................. 607/122 |
| 5,716,392 A | 2/1998 | Bourgeois et al. .......... 607/132 |
| 5,817,005 A | 10/1998 | Cohen |
| 5,827,216 A | 10/1998 | Igo et al. ...................... 604/21 |
| 5,868,770 A | 2/1999 | Rygaard ..................... 606/167 |

(Continued)

FOREIGN PATENT DOCUMENTS

WO   WO/0074574   12/2000

*Primary Examiner*—Beverly M. Flanagan
(74) *Attorney, Agent, or Firm*—Tom Berry; Jeffrey J. Hohenshell

(57) ABSTRACT

A tubular suction tool for accessing an anatomic surface or anatomic space and particularly the pericardium to access pericardial space and the epicardial surface of the heart to implant cardiac leads in a minimally invasive manner are disclosed. The suction tool incorporates a suction pad concave wall defining a suction cavity, a plurality of suction ports arrayed about the concave wall, and a suction lumen, to form a bleb of tissue into the suction cavity when suction is applied. The suction cavity extends along one side of the suction pad, so that the suction pad and suction cavity can be applied tangentially against a tissue site. The suction tool can incorporate light emission and video imaging of tissue adjacent the suction pad. A working lumen terminating in a working lumen port into the suction cavity enables introduction of tools, cardiac leads, and other instruments, cells, drugs or materials into or through the tissue bleb drawn into the suction cavity.

19 Claims, 23 Drawing Sheets

U.S. PATENT DOCUMENTS

| | | |
|---|---|---|
| 5,875,782 A | 3/1999 | Ferrari et al. ................ 128/898 |
| 5,972,013 A | 10/1999 | Schmidt ..................... 606/185 |
| 6,059,719 A * | 5/2000 | Yamamoto et al. ......... 600/127 |
| 6,080,175 A | 6/2000 | Hogendijk .................. 606/185 |
| 6,156,009 A | 12/2000 | Grabek ....................... 604/117 |
| 6,162,195 A | 12/2000 | Igo et al. |
| 6,231,518 B1 | 5/2001 | Grabek et al. .............. 600/508 |
| 6,251,092 B1 | 6/2001 | Qin et al. ................ 604/95.01 |
| 6,332,468 B1 | 12/2001 | Benetti ....................... 128/898 |
| 6,394,948 B1 | 5/2002 | Borst et al. .................... 600/37 |
| 6,423,051 B1 | 7/2002 | Kaplan et al. .............. 604/506 |
| 6,464,630 B1 * | 10/2002 | Borst et al. .................... 600/37 |
| 6,478,728 B1 | 11/2002 | Wright |
| 6,666,844 B1 | 12/2003 | Igo et al. |
| 6,837,848 B2 * | 1/2005 | Bonner et al. .............. 600/114 |
| 2002/0095139 A1 | 7/2002 | Jahns et al. |
| 2002/0138109 A1 | 9/2002 | Jahns et al. |

* cited by examiner

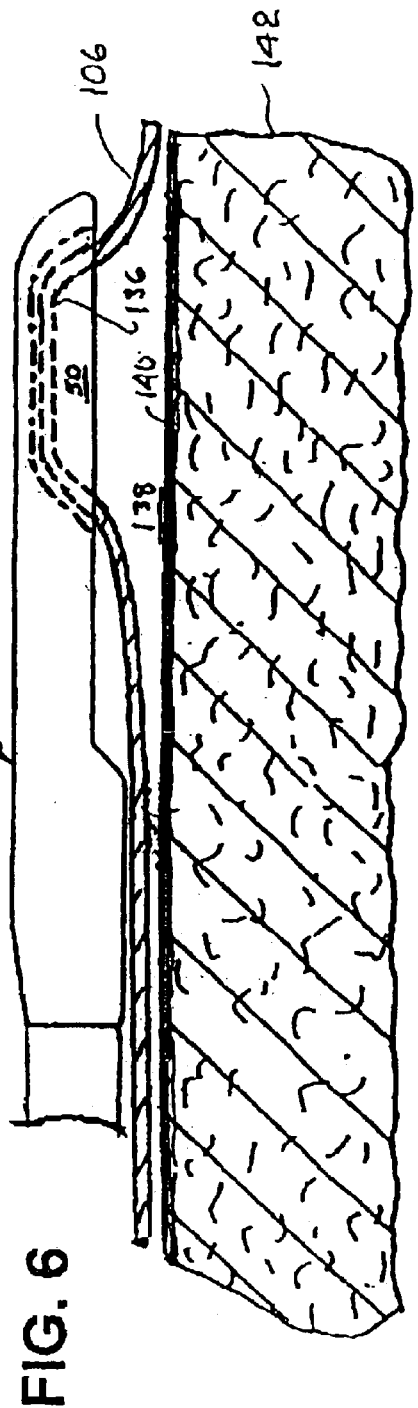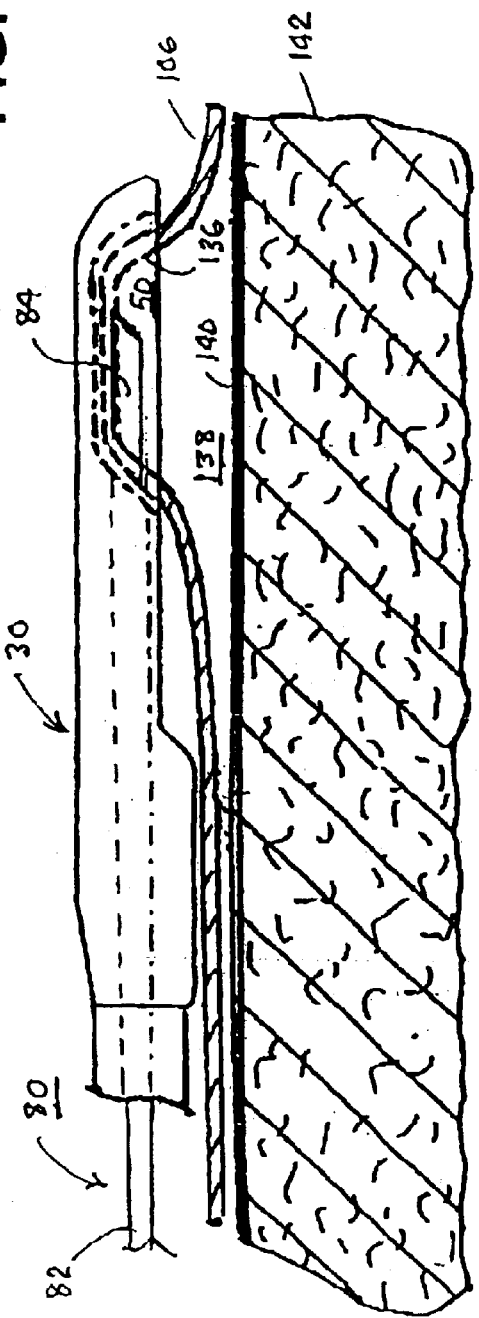

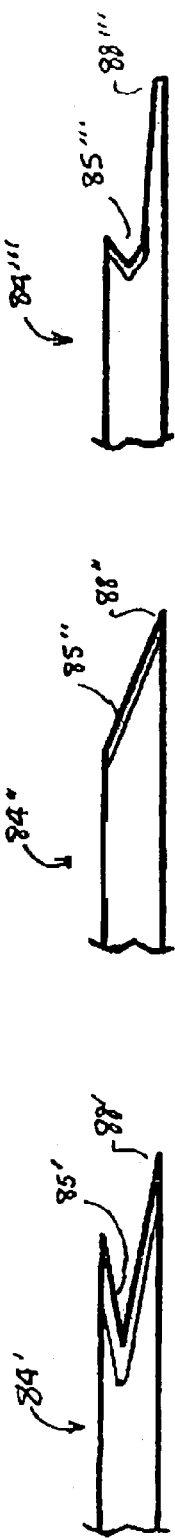
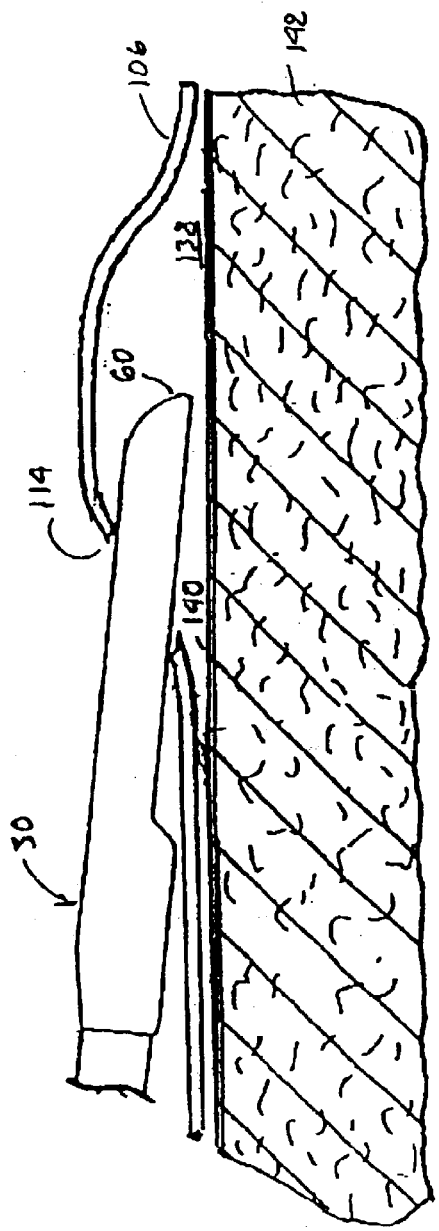

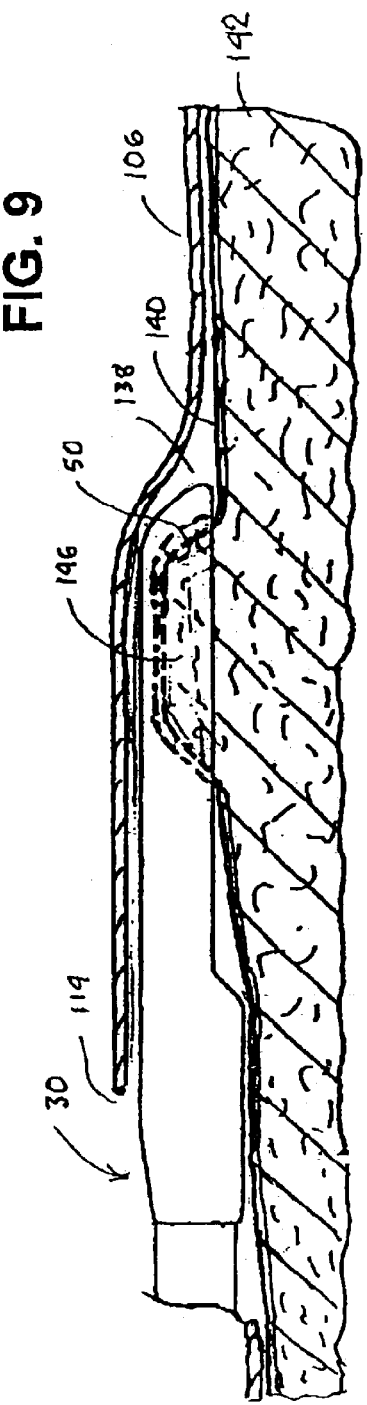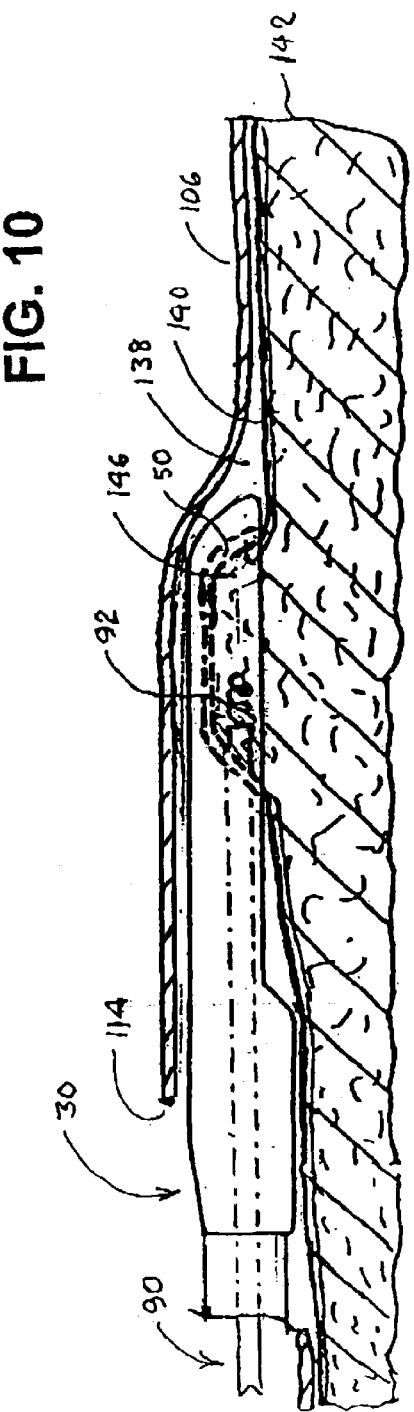

FIG. 11
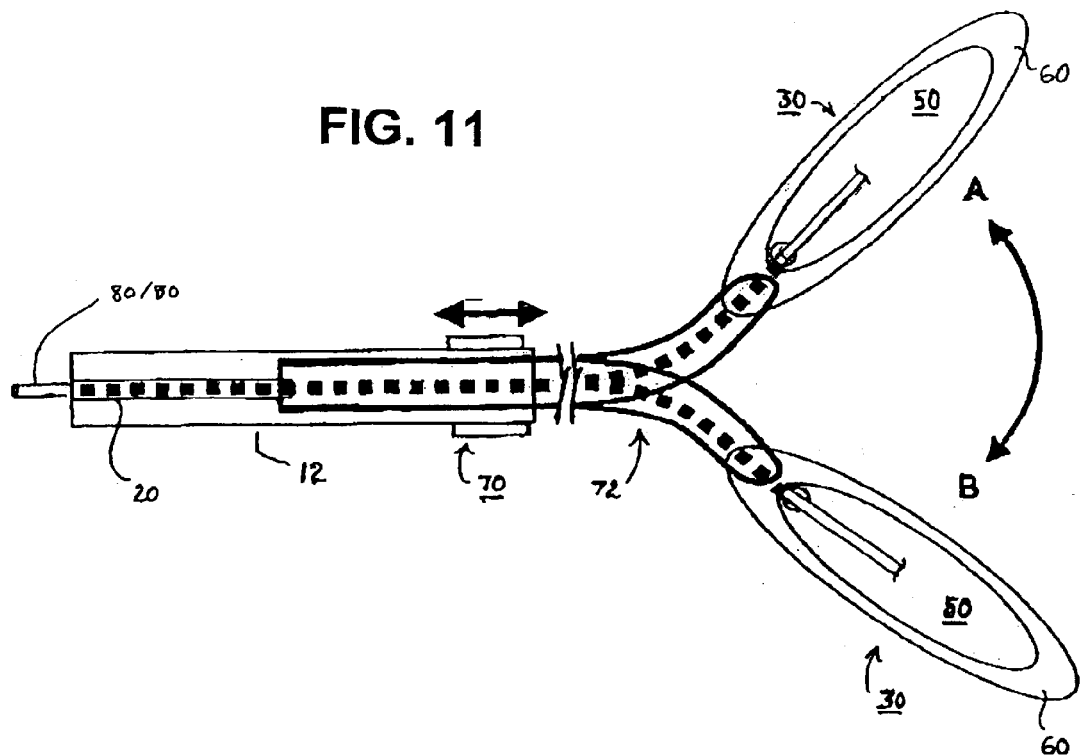
FIG. 12A     FIG. 13A     FIG. 14A
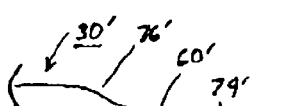    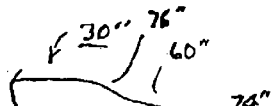    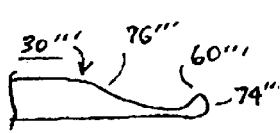
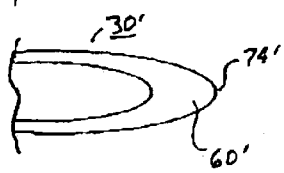    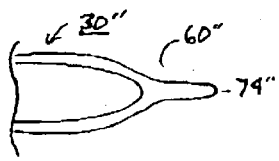    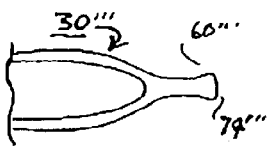
FIG. 12B     FIG. 13B     FIG. 14B

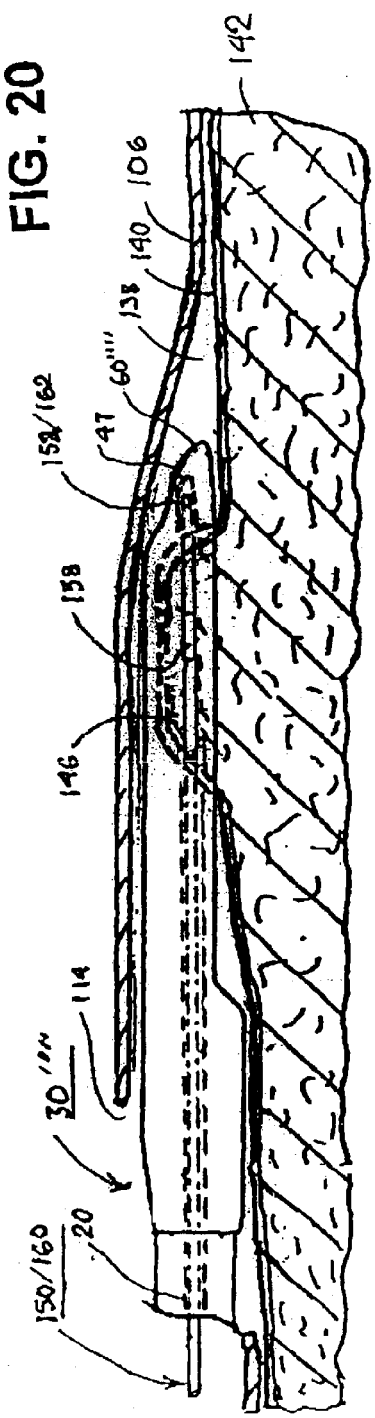
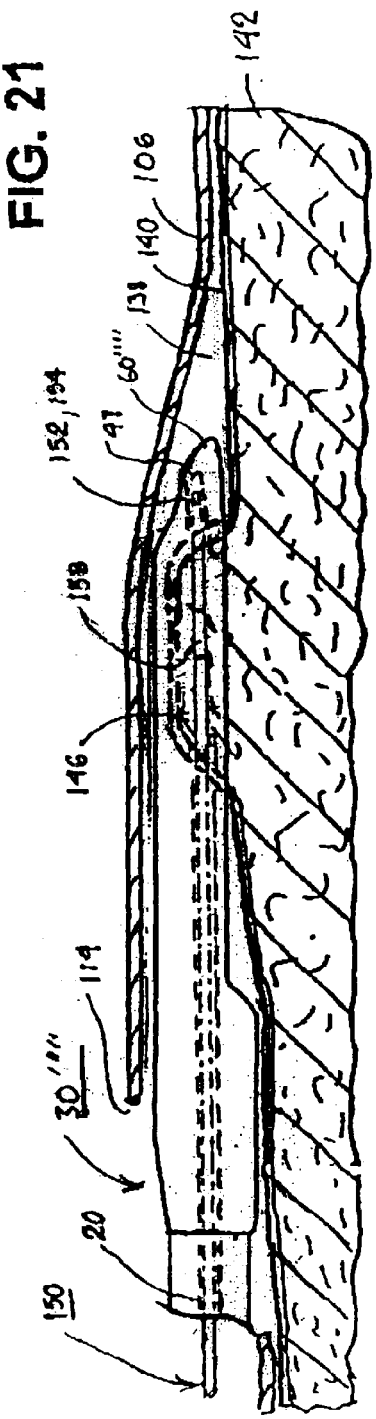

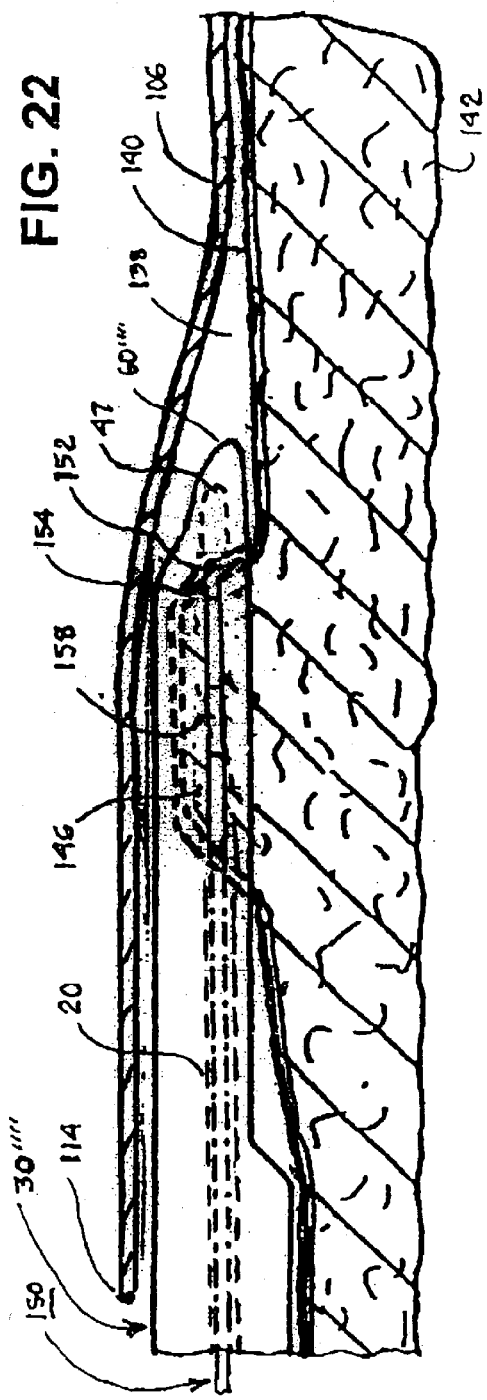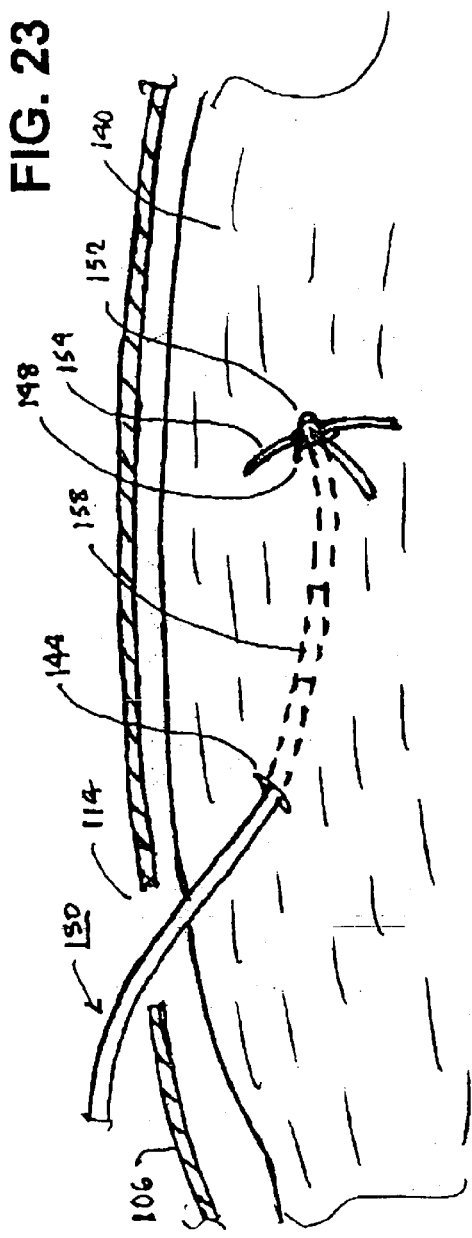

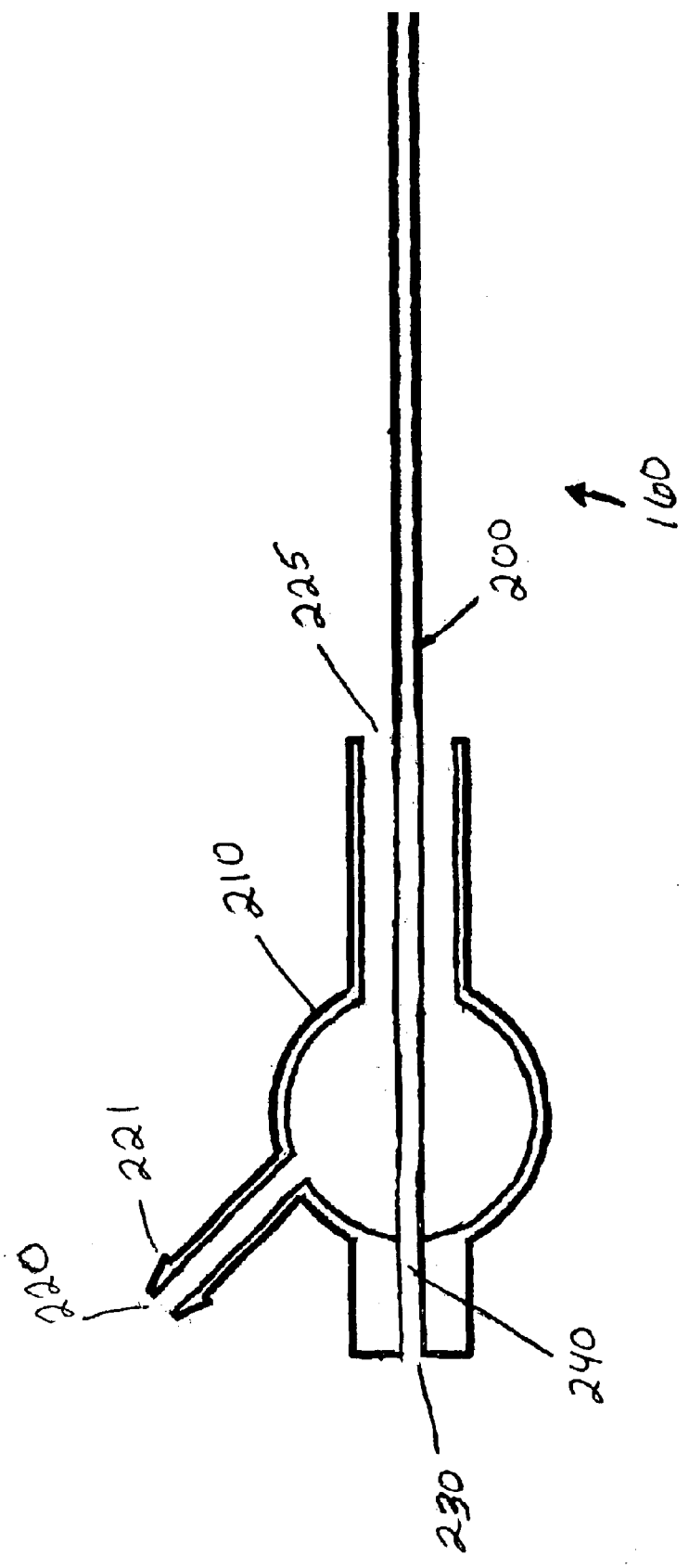

METHODS AND APPARATUS FOR ACCESSING AND STABILIZING AN AREA OF THE HEART

CROSS-REFERENCE TO RELATED APPLICATIONS

This application is a continuation-in-part of U.S. patent application Ser. No. 10/342,932 filed Jan. 15, 2003 now U.S. Pat. No. 6,837,848, the disclosure of which is incorporated herein by reference.

This application is related to commonly assigned U.S. patent application Ser. No. 10/283,794 filed Oct. 30, 2002, for METHODS AND APPARATUS FOR ACCESSING AND STABILIZING AN AREA OF THE HEART in the names of Gary W. Guenst et al., U.S. patent application Ser. No. 10/342,960 filed Jan. 15, 2003, for METHODS AND TOOLS FOR ACCESSING AN ANATOMIC SPACE in the name of Gary W. Guenst, and U.S. patent application Ser. No. 10/284,771 filed Oct. 31, 2002, for ANATOMIC SPACE ACCESS SUCTION TOOLS AND METHODS in the names of Koen Michels et al., the disclosures of which are incorporated herein by reference.

FIELD OF THE INVENTION

The present invention pertains to medical devices and methods for accessing an anatomic surface, muscle layer, vessel or anatomic space of the body and particularly for entering the pericardium to access pericardial space and the epicardial surface of the heart, particularly to implant a cardiac lead in a minimally invasive manner.

BACKGROUND OF THE INVENTION

The human heart wall consists of an inner layer of simple squamous epithelium, referred to as the endocardium, overlying a variably thick heart muscle or myocardium and is enveloped within a multi-layer tissue structure referred to as the pericardium. The innermost layer of the pericardium, referred to as the visceral pericardium or epicardium, clothes the myocardium. The epicardium reflects outward at the origin of the aortic arch to form an outer tissue layer, referred to as the parietal pericardium, which is spaced from and forms an enclosed sac extending around the visceral pericardium of the ventricles and atria. An outermost layer of the pericardium, referred to as the fibrous pericardium, attaches the parietal pericardium to the sternum, the great vessels and the diaphragm so that the heart is confined within the middle mediastinum. Normally, the visceral pericardium and parietal pericardium lie in close contact with each other and are separated only by a thin layer of a serous pericardial fluid that enables friction free movement of the heart within the sac. The space (really more of a potential space) between the visceral and parietal pericardia is referred to as the pericardial space. In common parlance, the visceral pericardium is usually referred to as the epicardium, and epicardium will be used hereafter. Similarly, the parietal pericardium is usually referred to as the pericardium, and pericardium will be used hereafter in reference to parietal pericardium.

It is frequently medically necessary to access the pericardial space to treat an injury, infection, disease or defect of the heart, e.g., an occluded coronary artery, a defective heart valve, aberrant electrical pathways causing tachyarrhythmias, bacterial infections, to provide cardiac resynchronization therapy, or to place epicardial pacing or cardioversion/defibrillation electrodes against the epicardium or into the myocardium at selected sites. It is necessary in these procedures to surgically expose and cut through the pericardium to obtain access to the pericardial space.

Highly invasive surgical techniques, referred to as a median sternotomy (open-chest surgical exposure) or a thoracotomy, have been typically employed to provide the surgeon access to the pericardial space and the heart. A median sternotomy incision begins just below the sternal notch and extends slightly below the xyphoid process. A sternal retractor is used to separate the sternal edges for optimal exposure of the heart. Hemostasis of the sternal edges is typically obtained using electrocautery with a ball-tip electrode and a thin layer of bone wax.

The open chest procedure involves making a 20 to 25 cm incision in the chest of the patient, severing the sternum and cutting and peeling back various layers of tissue in order to give access to the heart and arterial sources. As a result, these operations typically require large numbers of sutures or staples to close the incision and 5 to 10 wire hooks to keep the severed sternum together. Such surgery often carries additional complications such as instability of the sternum, post-operative bleeding, and mediastinal infection. The thoracic muscle and ribs are also severely traumatized, and the healing process results in an unattractive scar. Post-operatively, most patients endure significant pain and must forego work or strenuous activity for a long recovery period.

Many minimally invasive surgical techniques and devices have been introduced In order to reduce the risk of morbidity, expense, trauma, patient mortality, infection, and other complications associated with open-chest cardiac surgery. Less traumatic limited open chest techniques using an abdominal (sub-xyphoid) approach or, alternatively, a "Chamberlain" incision (an approximately 8 cm incision at the sternocostal junction), have been developed to lessen the operating area and the associated complications. In recent years, a growing number of surgeons have begun performing coronary artery bypass graft (CABG) procedures using minimally invasive direct coronary artery bypass grafting (MIDCAB) surgical techniques and devices. Using the MIDCAB method, the heart typically is accessed through a mini-thoracotomy (i.e., a 6 to 8 cm incision in the patient's chest) that avoids the sternal splitting incision of conventional cardiac surgery. A MIDCAB technique for performing a CABG procedure is described in U.S. Pat. No. 5,875,782, for example.

Other minimally invasive, percutaneous, coronary surgical procedures have been advanced that employ multiple small trans-thoracic incisions to and through the pericardium, instruments advanced through ports inserted in the incisions, and a thoracoscope to view the accessed cardiac site while the procedure is performed as shown, for example, in U.S. Pat. Nos. 6,332,468, 5,464,447, and 5,716, 392. Surgical trocars having a diameter of about 3 mm to 15 mm are fitted into lumens of tubular trocar sleeves, cannulae or ports, and the assemblies are inserted into skin incisions. The trocar tip is advanced to puncture the abdomen or chest to reach the pericardium, and the trocar is then withdrawn leaving the sleeve or port in place. Surgical instruments and other devices such as fiber optic thoracoscopes can be inserted into the body cavity through the sleeve or port lumens. As stated in the '468 patent, instruments advanced through trocars can include electrosurgical tools, graspers, forceps, scalpels, electrocauteries, clip appliers, scissors, etc.

In such procedures, the surgeon can stop the heart by utilizing a series of internal catheters to stop blood flow through the aorta and to administer cardioplegia solution.

The endoscopic approach utilizes groin cannulation to establish cardiopulmonary bypass (CPB) and an intraaortic balloon catheter that functions as an internal aortic clamp by means of an expandable balloon at its distal end used to occlude blood flow in the ascending aorta. A full description of an example of one preferred endoscopic technique is found in U.S. Pat. No. 5,452,733, for example.

However, recently developed, beating heart procedures disclosed in U.S. Pat. No. 6,394,948, for example, eliminate the need for any form of CPB, the extensive surgical procedures necessary to connect the patient to a CPB machine, and to stop the heart. These beating heart procedures can be performed on a heart exposed in a full or limited thoracotomy or accessed percutaneously.

In such percutaneous procedures, the epicardium of the beating or stopped heart is exposed to view typically by use of grasping and cutting instruments inserted through one port to cut through the pericardium surrounding the heart while the area is viewed through the thoracoscope or endoscope inserted through another port. The thoracoscopic approach typically requires the placement of a chest tube and admission to the hospital for the initial 1–2 postoperative days.

Therefore, much effort has been expended to develop medical devices and techniques to access the pericardial space employing such minimally invasive percutaneous procedures. One difficulty has been that normally the pericardial space is so small or thin that it is difficult to penetrate the pericardium using miniaturized instruments capable of being introduced through a port to the site without also puncturing the underling epicardium and thereby, damaging the myocardium or a coronary vessel. Proliferative adhesions occur between the pericardium and the epicardium in diseased hearts and hamper access to the pericardial space employing such minimally invasive percutaneous procedures. The simple percutaneous approach can be used to penetrate the pericardium to drain a large pericardial effusion, i.e., an accumulation of too much fluid in the pericardial space that widens the pericardial space. A spinal needle (18–20 gauge) and stylet occluding the needle lumen are advanced incrementally in a superior/posterior fashion through a small (2–4 mm) cutaneous incision between the xyphoid and costal cartilage. Periodically, the stylet is removed, and fluid aspiration is attempted through the needle lumen. The advancement is halted when fluid is successfully aspirated, and the pericardial effusion is then relieved.

Methods and apparatus for accessing the pericardial space for the insertion of implantable defibrillation leads are disclosed in U.S. Pat. Nos. 5,071,428 and 6,156,009, wherein a forceps device is used to grip the pericardium and pull it outward to form a "tent". In the '428 patent, a scissors or scalpel is introduced to cut the pericardium (pericardiotomy) under direct vision through a sub-xyphoid surgical incision. The forceps device disclosed in the '009 patent incorporates a mechanism for introducing electrical leads or guidewires through the outwardly displaced pericardium. It is difficult to introduce and use the forceps through the narrow lumen of a port or sleeve, particularly if the pericardial fluid is under pressure that makes the pericardium taut like an inflated balloon.

Further methods and apparatus for accessing the pericardial space for the insertion of devices or drugs are disclosed in U.S. Pat. No. 6,423,051, wherein an access tube having a device access lumen is provided with a plurality of hooks in the tube distal end that can be used to hook into the pericardium to enable the lifting and "tenting" of the pericardium. A cutting instrument or sharpened tip guidewire or the like can be advanced through the device access lumen to perforate the pericardium.

Other methods and apparatus that are introduced through percutaneously placed ports or directly through small transthoracic incisions for accessing the pericardial space employ suction devices to grip the pericardium or epicardium as disclosed, for example, in U.S. Pat. Nos. 4,991,578, 5,336, 252, 5,827,216, 5,868,770, 5,972,013, 6,080,175, and 6,231, 518 and the above-referenced '948 patent. The suction devices are configured like a catheter or tube having a single suction tool lumen and typically having a further instrument delivery lumen. The suction tool lumen terminates in a single suction tool lumen end opening through the device distal end in the '578, '252, '175, '770, and '013 patents and through the device sidewall in the '216 and '518 patents. Certain of these patents recite that the applied suction draws a "bleb," i.e., a locally expanded region of the pericardium, into the suction tool lumen or a suction chamber at the device distal end. A needle can then be advanced into the bleb and used to draw off fluids or deliver drugs into the pericardial space, or the like. In addition, it is suggested in these patents that treatment devices including catheters, guidewires, and electrodes, e.g., defibrillation electrodes, can be advanced into the pericardial space through a device introduction lumen for a variety of reasons. Although theoretically plausible, the ability to reliably maintain a vacuum seal against the pericardium when such treatment devices are advanced can be problematic.

For these reasons, it would be desirable to provide additional and improved methods and apparatus for the minimally invasive access to a patient's pericardial space. The methods and devices should be suitable for a wide variety of minimally invasive approaches to the pericardium, including at least intercostal/transthoracic and subxiphoid approaches, and the like. The methods and devices should further provide for secure and stable capture of the pericardium and permit the opening of a large space or volume between the pericardium and epicardium. Such access methods and apparatus should be useful for a wide variety of procedures to be performed in the pericardial space, including fluid withdrawal, drug delivery, cell delivery, diagnostic and therapeutic electrophysiology procedures, pacemaker lead implantation, defibrillator lead placement, transmyocardial revascularization, transmyocardial revascularization with drug delivery, placement of the left ventricular assist devices, placement of the arterial bypass graphs, in situ bypass, i.e., coronary artery-venous fistulae, placement of drug delivery depots, closure of the left arterial appendage, and the like. At least some of these objectives will be met by the invention described herein.

SUMMARY OF THE INVENTION

In accordance with a preferred embodiment of the present invention, an elongated suction tool is introducible through a percutaneous pathway, e.g., through the lumen of a percutaneous sleeve extending from the skin to a lateral surface of a tissue site. The suction tool incorporates a suction pad concave wall defining a suction cavity, a plurality of suction ports arrayed about the concave wall, and a suction lumen, to form a bleb of tissue into the suction cavity when suction is applied. The suction cavity extends along one side of the suction pad, so that the suction pad and suction cavity can be applied tangentially against a tissue site.

Preferably, the suction tool incorporates one or more light emitter to illuminate the tissue, a camera or a light pipe to an external video camera and display to image the illuminated tissue, and a working lumen terminating in a working lumen port into the suction cavity to introduce tools, cardiac leads, and other instruments, drugs or materials into or through the tissue bleb drawn into the suction cavity.

In accordance with a further aspect of the invention, the suction pad distal end is shaped to form a tissue dilator to be inserted through an incision made through the tissue to facilitate advancement of the suction pad through the incision.

In accordance with a still further aspect of the invention, the distal suction pad and a distal segment of the suction tool body are deflectable to steer the suction pad to a desired illuminated and imaged tissue site, e.g., a site of the pericardium or the epicardium.

The methods, suction tool and tool kits of the present invention can advantageously be used to access the pericardial space between the pericardium and epicardium. Various tools and devices can be introduced into the pericardial space for temporary treatment of the pericardial space or myocardium or to complete a cardiac surgical procedure or for permanent implantation against the epicardium or within the pericardial space or within the myocardium or within a coronary vein or artery.

One aspect of the present invention provides methods, apparatus, and kits for accessing a patient's pericardial space between the pericardium and the epicardium in a minimally invasive manner to enable implantation of a cardiac lead electrode through the pericardium and upon the epicardium or into the myocardium. The present invention will be also be useful for accessing the pericardial space for performing a wide variety of procedures, generally as set forth above, separately or ancillary to the implantation of the cardiac lead electrode.

In an exemplary cardiac lead implantation, the suction pad is laterally extended out of the percutaneous sleeve lumen distal end opening and applied tangentially against the pericardial surface. The light source and camera/video display are employed to visualize the positioning of the suction pad against the pericardium. Suction is applied through the suction lumen and suction ports to form a bleb of the pericardium into the suction cavity of the suction pad. A cutting instrument is introduced through the working lumen into the suction cavity to make an incision through the pericardial bleb. Other cutting or shaping instruments can be introduced through the working lumen port to lengthen the pericardial incision.

The cutting instrument can be a knife blade, a needle, a stiff guidewire tip, an electrosurgical cutting tool, surgical scissors, or other piercing or cutting tools. Preferably, the cutting instrument comprises a shaped cutting blade having a blade tip and a blade edge that facilitates perforating and cutting a slit through the pericardium to form an elongated pericardial incision.

At this point, the pericardial space is accessed, and the suction pad of the suction tool can be advanced into the pericardial space. The pericardial space can be illuminated and visualized employing the light source and camera/video display. Various tools, instruments, drugs, other materials and devices can be introduced through the working lumen into the illuminated and imaged pericardial space. For example, a distal portion of a cardiac lead can be introduced into the pericardial space to dispose one or more electrode, e.g., a large surface area cardioversion/defibrillation electrode or indifferent pace/sense electrode, into the pericardial space to lodge against the epicardium.

The suction tool can be advanced through the pericardial incision to dispose the suction pad into lateral engagement with the epicardium. Again, the light source and camera/video display are employed to visualize the positioning of the suction pad against the epicardium. Suction is again applied to grip the epicardium and form a bleb of the myocardium within the suction cavity of the suction pad.

Thus, in accordance with yet another aspect of the invention, the suction tool can be employed to both form a pericardial bleb and a myocardial or myocardial bleb in succeeding steps of a method of accessing the pericardial space and affixing a cardiac lead electrode against the epicardium or in the myocardium.

One preferred use of the suction tool is to enable implantation of an epicardial cardiac lead having a fixation mechanism that is lodged into or through the myocardium into a heart chamber or tangentially through the myocardial bleb and against the epicardium. The fixation mechanism of such a cardiac lead is advanced through the working lumen and inserted into or through the myocardium to fix a pace/sense electrode in intimate contact with the myocardium or against the epicardium. The fixation mechanism can comprise, for example, a barbed hook that is pushed into the myocardium or a helix that is screwed into the myocardium. The hook or helix can be formed of an electrically conductive material to function as a pace/sense electrode in a manner well known in the art.

In a further variation of the suction tool, a suction cavity distal slot or recess can be provided in the distal end wall of the suction cavity that is generally aligned with the working lumen port. The distal recess can receive and act as a stop for the blade tip of the cutting blade and can also be employed to facilitate deployment of particular cardiac lead fixation mechanisms.

In the latter case, the distal recess receives the distal end of a cardiac lead and cardiac lead installation tool that is pushed through the myocardial bleb to dispose the cardiac lead distal end distal to a distal epicardial perforation. The distal end of a cardiac lead having a deployable distal fixation mechanism restrained by the installation tool can thereby be advanced through the myocardial bleb. The lead installation tool is manipulated to deploy the distal fixation mechanism within the suction cavity and against the epicardium, and the installation tool is then retracted over the lead body through the working lumen. Suction is released, and the suction tool is then retracted over the cardiac lead.

The suction tool body and/or the working lumen can be circular or oval or have any other desirable cross-section shape. The suction tools of the present invention can have a non-circular cross-section to fit a non-circular cross-section working lumen so as to optimize the shape of the suction pad and suction cavity and to ensure that the cutting instrument does not rotate within the working lumen as it is advanced therethrough and used to make the tissue incision.

The tubular suction tool body can be straight, curved or formed with a bend or formed of a bendable material to be shaped by the user. The suction cavity of the suction pad can be relatively elongated in axial alignment with the suction tool body, e.g., in the shape of a closed or open-ended half-pipe, or can be hemispheric in shape.

Advantageously, there is no suction applied through the working lumen that is necessary to maintain the attachment to the pericardium or epicardium while it is being perforated or while other devices or materials of the types described above are advanced through working lumen to make or pass through the incision or perforation. Moreover, it is simpler to advance such cutting instruments, cardiac leads, other devices and materials through the working lumen from a proximal lumen end opening that is exposed to the atmosphere.

This summary of the invention has been presented here simply to point out some of the ways that the invention overcomes difficulties presented in the prior art and to distinguish the invention from the prior art and is not intended to operate in any manner as a limitation on the interpretation of claims that are presented initially in the patent application and that are ultimately granted.

BRIEF DESCRIPTION OF THE DRAWINGS

These and other advantages and features of the present invention will be more readily understood from the following detailed description of the preferred embodiments thereof, when considered in conjunction with the drawings, in which like reference numerals indicate identical structures throughout the several views, and wherein:

FIG. 6 is a schematic illustration of the application of suction through the suction ports of the suction pad to form a pericardial bleb;

FIG. 7 is a schematic illustration of the advancement of a cutting instrument through the working lumen of the suction tool and through the pericardium while suction continues to be applied through the suction ports of the suction pad to maintain the pericardial bleb;

FIG. 8 is a schematic illustration of the advancement of the suction tool through the incision made through the pericardium;

FIG. 9 is a schematic illustration of the application of suction through the suction ports of the suction pad against the epicardium to form a myocardial bleb;

FIG. 10 is a schematic illustration of the advancement of a cardiac lead through the working lumen of the suction tool and rotation of the lead body to screw the fixation helix of the cardiac lead into the myocardium;

FIG. 11 is a schematic illustration of a modification of the suction tool providing for the capability of deflecting the suction pad to steer it to a particular pericardial or epicardial site and to orient the suction cavity to the pericardium or epicardium to form a respective pericardial or myocardial bleb;

FIGS. 12A and 12B are schematic illustrations of a first alternate shape of the suction tool distal end to facilitate advancement through and widening of the incision in the pericardium as depicted in FIG. 8;

FIGS. 13A and 13B are schematic illustrations of a second alternate shape of the suction tool distal end to facilitate advancement through and widening of the incision in the pericardium as depicted in FIG. 8;

FIGS. 14A and 14B are schematic illustrations of a first alternate shape of the suction tool distal end to facilitate advancement through and widening of the incision in the pericardium as depicted in FIG. 8;

FIG. 15 is a schematic illustration of one shape of a cutting instrument blade of the cutting instrument advanced through the working lumen to form the incision through the pericardium as depicted in FIG. 7;

FIG. 16 is a schematic illustration of a further shape of a cutting instrument blade of the cutting instrument advanced through the working lumen to form the incision through the pericardium as depicted in FIG. 7;

FIG. 17 is a schematic illustration of a still further shape of a cutting instrument blade of the cutting instrument advanced through the working lumen to form the incision through the pericardium as depicted in FIG. 7;

FIG. 20 is a schematic illustration of the application of suction through the suction ports of the suction pad of FIGS. 18–19 against the epicardium to form a myocardial bleb, and the advancement of a cardiac lead within a lead installation tool through the working lumen of the suction tool and the myocardial bleb;

FIG. 21 is a schematic illustration of the cardiac lead of FIG. 20 lodged within the myocardial bleb upon retraction of the lead installation tool;

FIG. 22 is a schematic illustration of the cardiac lead of FIG. 20 lodged within the myocardial bleb a distal fixation mechanism of the cardiac lead deployed against the epicardium distal to a distal epicardial perforation upon retraction of the lead installation tool; and FIG. 23 is a schematic illustration of the cardiac lead of FIGS. 20–22 attached to the myocardium following removal of the suction tool.

FIG. 24 is a schematic illustration of a cardiac lead installation tool.

Figure 1:
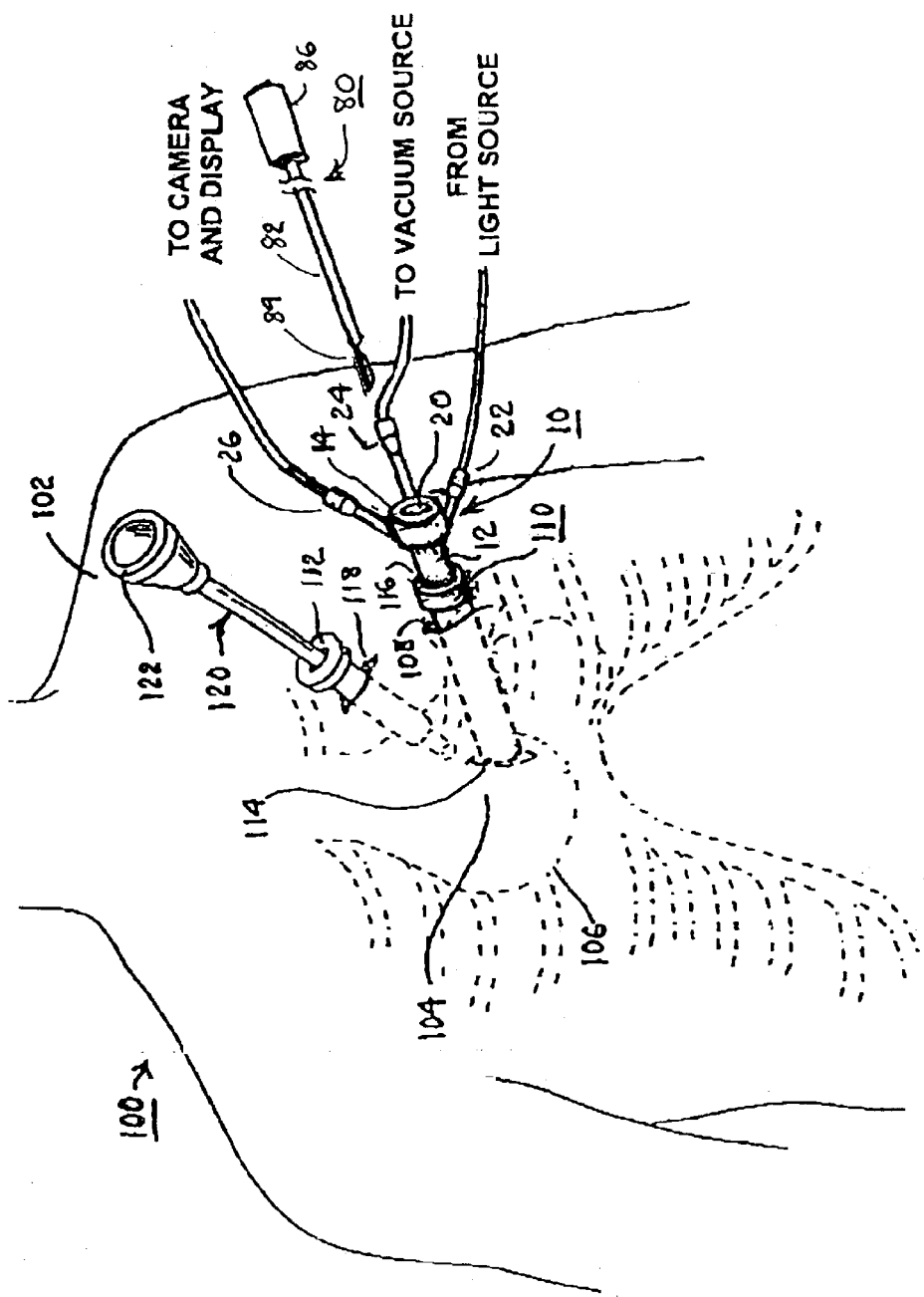
FIG. 1 is an illustration of the preparation of a patient for accessing the pericardial space through the use of a suction tool of the present invention introduced through the sleeve lumen of a percutaneously placed tubular access sleeve in preparation for advancement of a cutting instrument through the working lumen of the suction tool for making an incision through the epicardium.

The drawing figures are not necessarily to scale.

DETAILED DESCRIPTION OF THE PREFERRED EMBODIMENTS

In the following detailed description, references are made to illustrative embodiments of methods and apparatus for carrying out the invention. It is understood that other embodiments can be utilized without departing from the scope of the invention. Preferred methods and apparatus are described for accessing the pericardial space between the epicardium and the pericardium as an example of accessing an anatomic space between an outer tissue layer and an inner tissue layer.

Figure 2:
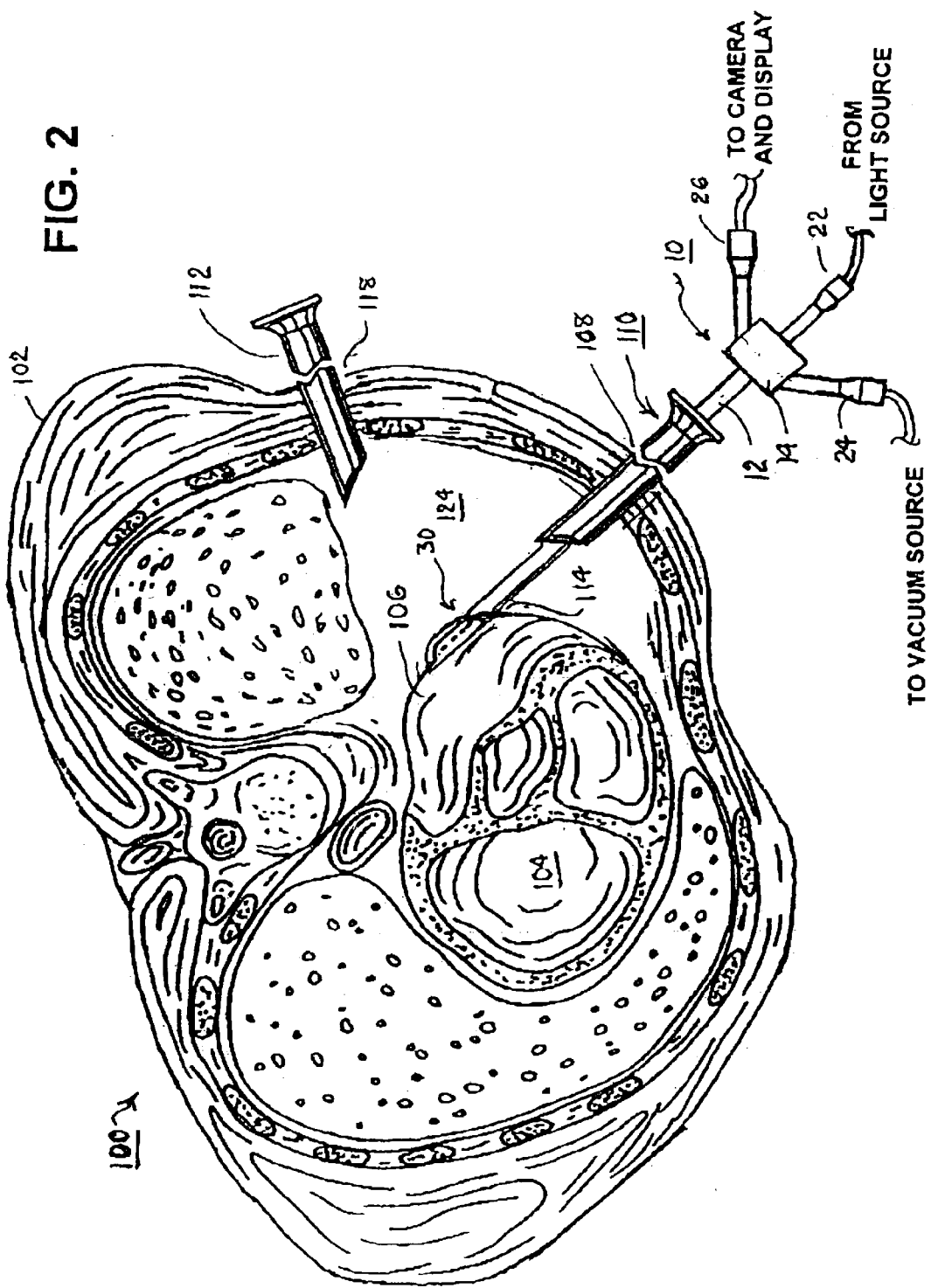
FIG. 2 is cross-section view of the patient's thorax depicting the advancement of the suction pad at the suction tool distal end against the pericardium.
Figure 3:
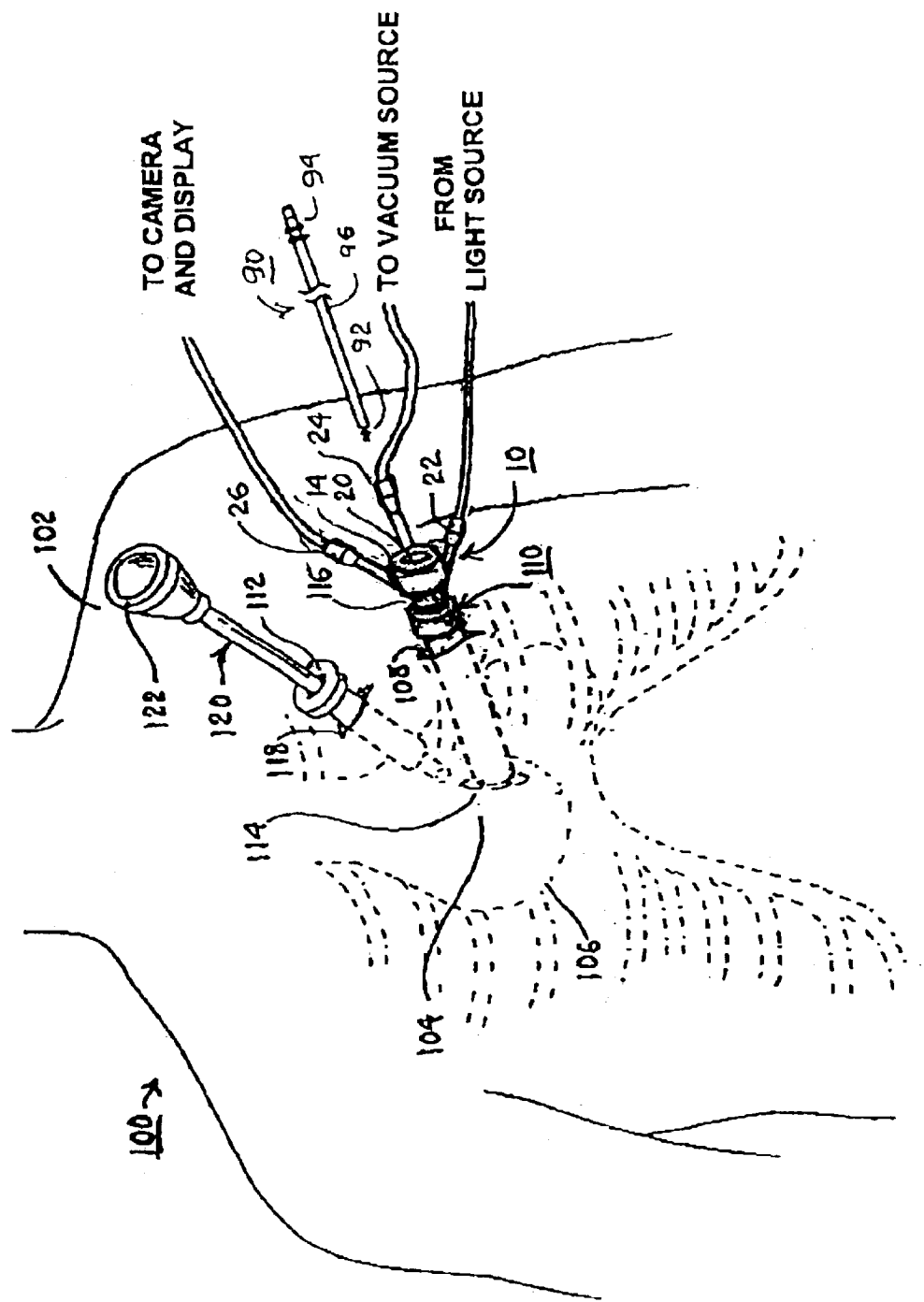
FIG. 3 is an illustration of the advancement of the suction tool within the sleeve lumen when the distal suction pad of the suction tool is advanced through an incision in the pericardium in preparation for advancement of a cardiac lead through the working lumen of the suction tool to enable screwing of a fixation helix of the cardiac lead into the myocardium.

For example, FIGS. 1–3 illustrate the placement of instruments through the chest wall of a patient 100 for observation and accessing the pericardial space through an incision in the pericardium 106 exposing the pericardium of the heart 104 to perform any of the ancillary procedures listed above. The patient 100 is placed under general anesthesia, and the patient's left lung is deflated if necessary, using conventional techniques. The patient 100 is placed in a lateral decubitus position on his right side, and small percutaneous incisions are to be made in the skin 102 through the chest wall for the receipt of surgical instruments. As used herein, the term "percutaneous" refers to any penetration through the skin of the patient, whether in the form of a small cut, incision, hole, cannula, tubular access sleeve or port or the like, that is preferably made in an interstitial space between the ribs of the patient 100.

First and second passages 108 and 118 are preferably made through the skin 102 into the thoracic cavity. The passages 108 and 112 are typically formed employing one-piece rods or trocars of prescribed diameters and lengths that are advanced through body tissue to form the passage and then removed so that other instruments can be advanced through the passage. The passage can also be formed employing two piece trocars that comprise a tubular outer sleeve, sometimes referred to as a port or cannula or at times as the tubular access sleeve itself, having a sleeve access lumen extending between lumen end openings at the sleeve proximal end and sleeve distal end, and an inner puncture core or rod that fits within the sleeve access lumen. The inner puncture rod typically has a tissue penetrating distal end that extends distally from the sleeve distal end when the inner puncture rod is fitted into the sleeve access lumen for use. The two-piece trocar can be assembled and advanced as a unit through body tissue, and the inner puncture rod then removed leaving the tubular access sleeve in place to maintain a fixed diameter passage through the tissue for use by other instruments.

In one of these ways, a tubular access sleeve 110 is placed through first passage 108 that is made as described above in the chest wall of patient 100 between the patient's 2nd rib and 6th rib, for example. The selection of the exact location of the first passage 108 is dependent upon a patient's particular anatomy. A further conventional tubular access sleeve 112 is shown left in place in a second passage 110 that is made as described above in the chest wall of patient 100.

Typically, the patient's left lung is deflated to allow unobstructed observation of the pericardium 106 employing a thoracoscope 120 inserted through a sleeve lumen of tubular access sleeve 112. Frequently, the deflation is accomplished by use of a double lumen endotracheal tube that is inserted into the trachea, and independent ventilation of the right, left or both lungs can be selected. The left lung will collapse for visualization of the structures of the left hemi-sternum when ventilation of the left lung is halted and the left thoracic negative pressure is relieved through a lumen of the tubular access sleeve 112 or a further access sleeve to atmospheric pressure. After deflation, the thoracic cavity may be suffused with a gas, e.g., carbon dioxide, introduced through a lumen of the tubular access sleeve 112 or the further access sleeve to pressurize the cavity to keep it open and sterile. The pressurized gas keeps the deflated lung away from the left heart so that the left heart can be viewed and accessed and provides a working space for the manipulation of the tools of the present invention. It will be understood that the access sleeve lumens must be sealed with seals about instruments introduced through the lumens to maintain the pressurization.

A thoracoscope 120 can then inserted into the lumen of the tubular access sleeve 112 to permit wide angle observation of the thoracic cavity by a surgeon directly through an eyepiece 122 or indirectly through incorporation of a miniaturized image capture device, e.g., a digital camera, at the distal end of the thoracoscope 120 or optically coupled to the eyepiece 122 that is in turn coupled to an external video monitor (not shown). The thoracoscope 120 also incorporates a light source for illuminating the cavity with visible light so that the epicardial surface can be seen directly or indirectly. The depicted thoracoscope 120 is used to directly visualize the thoracic cavity and obtain a left lateral view of the pericardial sac or pericardium 106 over the heart 104.

The elongated access sleeve 110 provides an access sleeve lumen 116 enabling introduction of suction tool 10 to dispose the suction pad 30 within the thoracic cavity. The tubular access sleeve 110 and suction tool 10 of the present invention are employed to access the pericardium 106 and to grip its surface to tension it so that an incision can be made through the pericardium 106. The accessed pericardial space 124 and epicardium 106 surrounding the heart 104 are shown more specifically in the cross-section view of FIG. 2. A cutting instrument 80, e.g., a knife, a needle, a stiff guidewire tip, an electrosurgical cutting tool, surgical scissors, or other piercing or cutting instrument 80 is depicted in FIG. 1 poised to be inserted through the suction tool working lumen 20 to perforate a bleb of pericardium 106 within the suction cavity of the suction pad 30 and then form a pericardial incision 114 through the pericardial bleb exposing the pericardial space and exterior surface of the epicardium of the heart 104. Exemplary cutting blades that can be employed in cutting instrument 80 are disclosed herein.

The suction pad 30 is advanced through the incision formed through the pericardium and against the epicardium. In one preferred use of the suction tool of the present invention, a myocardial bleb is formed by the applied suction so that an epicardial lead can be attached to the myocardium by a fixation mechanism. An exemplary cardiac lead 90 having a distal fixation helix 92 that may also function as a pace/sense electrode is depicted in FIG. 3 poised to be advanced through the working lumen 20. The cardiac lead can take any of the forms known in the pacing art having one or more distal pace/sense electrodes coupled through one or more respective conductors within lead body 96 extending to one or more respective connector elements of a proximal connector assembly 94. Preferably the outer diameters of the distal fixation mechanism 92, the proximal connector assembly 94 and the lead body 96 are approximately the same or smaller and fit through the working lumen 20. The distal fixation mechanism 92 can comprise a fixation helix, prong or hook or can take other forms, and further examples are described below.

Figure 4:
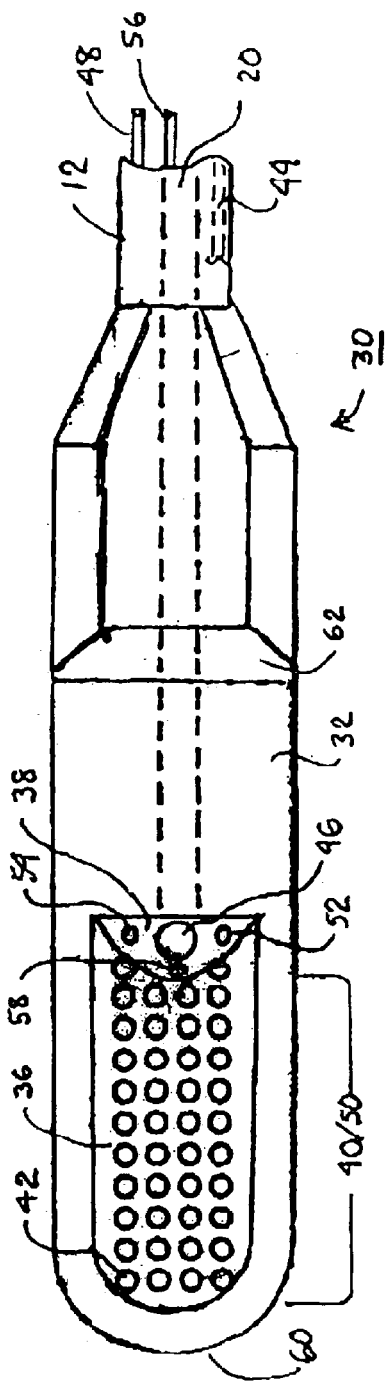
FIG. 4 is a plan view of the distal suction pad of the suction tool of FIGS. 1–3.
Figure 5:
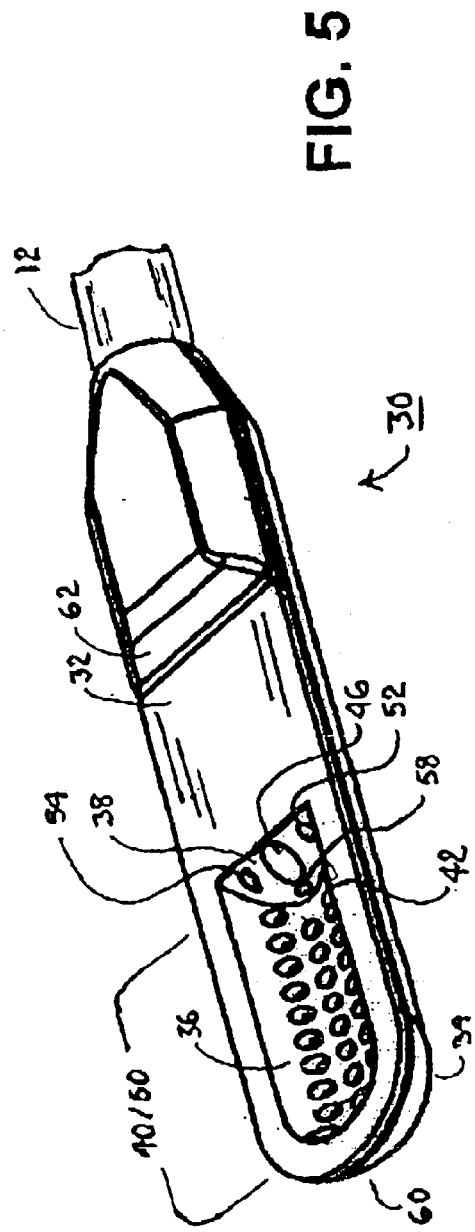
FIG. 5 is a perspective view of the distal suction pad of the suction tool of FIGS. 1–3.

The suction tool 10 comprises a suction tool body 12 extending between a proximal suction tool port assembly 14 and a suction pad 30 depicted in greater detail in FIGS. 4 and 5. The suction tool body 12 and the distal suction pad 30 are sized to be inserted through an incision or the access sleeve lumen 116 so that the suction pad 30 can first be introduced into the thoracic cavity and applied against the epicardium, then advanced through an incision made in the epicardium, and then applied against the myocardium.

The suction tool proximal assembly 14 comprises the proximal end opening of the suction tool working lumen 20, an optical or electrical illumination connector 22, a vacuum side port 24, and an optical or electrical imaging connector 26.

The vacuum side port 24 is adapted to be attached to a vacuum source at the surgical site to draw suction through one or more vacuum lumen extending through the suction tool proximal end assembly 14, the suction tool body 12 and then through a plurality of suction ports 42 of suction port array 40 depicted in FIGS. 4 and 5.

In accordance with one aspect of the present invention, the tissue sites, i.e., the pericardium, pericardial space and myocardium in this instance, adjacent to the suction pad are optionally illuminated and imaged through the suction tool 10. The illumination of the sites can be accomplished by one or more miniaturized light emitters incorporated into the suction pad 30 coupled to conductors extending through the tool body 12 to an electrical illumination connector 22 that is coupled to an external battery pack or the like. However, for safety, economic, and space reasons, it is preferred that light be conducted from an external light source to the suction pad 30. So, it will be understood that the suction tool 10 incorporates an optical illumination connector 22 including one or more fiber-optic light pipes extending to one or more light emitting lens elements and/or light pipe ends, e.g., light pipe ends 52 and 54 depicted in FIGS. 4 and 5. The light pipe ends 52 and 54 can be polished or surface treated to enhance dispersion of light and light brightness.

The illuminated tissue site could be imaged by incorporating a miniaturized video camera digital imaging array and lens in the suction pad 30 and powering the array and conducing image pixel data through conductors extending to an electrical imaging connector 26 to be coupled to external video imaging and display apparatus. However, for safety, economic, and space reasons, it is preferred that an image of the illuminated site be optically conveyed from an external light source to the suction pad 30. Again, it will be understood that the suction tool 10 incorporates an optical imaging connector 26 coupled with a fiber-optic light pipe extending to an imaging lens element or pipe end 38 depicted in FIGS. 4 and 5. The light pipe end 58 can be polished or shaped to function as a lens.

One preferred configuration of the non-conductive suction pad 30 is depicted in FIGS. 4 and 5. The suction pad 30 features a flat lower wall 32, a convex upper wall 34, a concave suction pad wall 36 extending into the flat wall 32 toward the convex upper wall 34 and a proximal cavity wall 38, whereby a suction cavity 50 is created that a bleb of tissue can be drawn into. A suction port array 40 comprises a plurality of suction ports 42 through the concave suction pad wall 36 from an interior manifold coupled with a suction lumen 44 extending the length of the tool body 12 to the suction side port 24. The orientation of the suction cavity 50 to the axis of the tool body 12 allows the suction cavity to be advanced tangentially to the surface of the tissue that is approached to be drawn into the suction cavity 50 as a tissue bleb.

The working lumen 20 extends through the tool body 12 and a proximal portion of the suction pad 30 to a working lumen port 46 in the proximal cavity wall 38 defining the suction cavity 50. Therefore, the various instruments such as cutting instrument 80 and cardiac lead 90 referred to herein can be advanced tangentially into the tissue bleb.

It should be noted that the working lumen 20 can also be the suction lumen 44 in suction tools specifically designed to introduce medical instruments and devices, rather than fluids or materials, through the combined lumen. Suction would then be applied to the tissue bleb through the working lumen port 46 as well as the array of suction ports Optionally, an illumination light pipe 48 extends from the optical illumination connector 22 through the length of the tool body 12 and branches within the proximal portion of the suction pad 30 to a pair of illumination light pipe ends 52 and 54 in proximal suction pad wall 38. Similarly, optionally, an imaging light pipe 56 extends from the optical imaging connector 26 through the length of the tool body 12 and the proximal portion of the suction pad 30 to an imaging light pipe end 58 in proximal cavity wall 38. Therefore, the area within the concave suction wall 36 and distal to the suction pad distal end 62 can be illuminated and imaged remotely. It should be noted that the light pipes 48 and 56 can be extended past the suction cavity 50 to terminate with the light pipe ends 52, 54 and 56 arrayed near the suction pad distal end 60. Or, the light pipes can extend simply to the more proximal suction pad wall 62 and terminate with the light pipe ends 52, 54 and 56 arrayed in the more proximal suction pad wall 62.

In use, the suction pad 30 is laterally extended out of the suction tool lumen 20 so that a tangential approach can be made to the tissue, such as the pericardium 106 as shown in FIG. 2. The area is optionally illuminated and imaged as described above, and suction is applied to draw a pericardial bleb 136 into the suction cavity 50 as shown in FIG. 6. The pericardial space 138 can then be tented away from the heart 104.

In FIG. 7, the cutting instrument 80 is advanced through the working lumen 20 and the blade 84 is advanced out of the working lumen port 46 through a pericardial perforation and along the pericardium 106 to form the pericardial incision 114. The length of the pericardial incision 114 generally corresponds to the length of the suction cavity 50. The pericardial incision therefore has a perimeter that is larger than the perimeter of the cross section of the suction pad 30, enabling the suction pad to be advanced through the pericardial incision 114.

Advantageously, there is no suction applied through the suction tool working lumen 20 that is necessary to maintain the attachment of the pericardium 106 while it is being cut to form the pericardial incision 114 to reach the pericardial space 138. Due to their redundancy, the plurality of suction ports 42 of the suction pads 30 provide more robust fixation to the pericardium 106 (or other outer tissue layer) than a single large area suction port. At least some of the suction ports 42 readily engage the pericardial surface under low suction force to maintain the pericardial bleb 136 and enable lifting of the pericardium 106 or tracking movement of the pericardium 106. Engagement of the surface of the pericardium 106 by all of the suction ports 42 is not necessary. Similarly, the loss of engagement of some of suction ports 42 with the surface areas of the pericardium 106 does not result in complete loss of engagement as is the case when an edge of a single large suction port releases from a tissue surface of an outer tissue layer or the pericardium.

Furthermore, the suction tool 10 is versatile in that it can be used to simply access the pericardial space 138. Various instruments, medical devices, drugs or materials can be advanced through the working lumen 20, out of the working lumen port 46, through the pericardial incision 114, and into the pericardial space 138 for temporary treatment of the heart 104 or pericardial space 138 or to complete a surgical procedure or for permanent implantation of medical devices against the epicardium 140 or within the pericardial space or within the myocardium 142 or within a coronary vein or artery.

However, a preferred use of the suction tool 10 to enable implantation of the cardiac lead 90 is further illustrated in FIGS. 8–10. The cutting instrument 80 is withdrawn from the working lumen 20, and the pericardial bleb 136 is released from the suction cavity 50. The suction tool 10 is manipulated to insert the suction pad distal end 60 into the illuminated and imaged pericardial incision 114 as shown in FIG. 8. The suction pad 30 is inserted through the pericardial incision 114 and advanced into the pericardial space 138 with the suction cavity 50 facing the epicardium 140. Suction is then restored through the suction ports 42, and a myocardial bleb 146 is drawn into the suction cavity 50 as shown in FIG. 9.

The cardiac lead 90 is then advanced through the working lumen 20 to dispose the active fixation helix 92 at the working lumen port into the suction cavity 50. The cardiac lead body is then rotated at the proximal connector assembly in the proper direction to screw the fixation helix 92 through the epicardium 140 and into the myocardial bleb 146. Sensing and pacing threshold measurements are made in the conventional manner. The suction tool 10 is withdrawn over the lead body if acceptable thresholds are realized. The fixation helix 92 can be released if the thresholds are not acceptable, and the process of FIGS. 7–10 repeated until an acceptable site is found. The lead body is routed to the implantation site of an implantable pulse generator (IPG), and the lead connector assembly is coupled to the IPG in the conventional manner.

In accordance with a still further aspect of the invention, the suction tool 10 is equipped with a steering mechanism that the surgeon can manipulate at the suction tool proximal end assembly 14 to steer the suction pad 30 to a desired illuminated and imaged tissue site, e.g., a site of the pericardium or the epicardium illustrated in FIGS. 6–10. Such a capability is schematically depicted in FIG. 11. A deflection mechanism 70 can be incorporated into the suction tool body 12 that the user can manipulate to induce a bend in a distal segment 72 of suction tool body 12 to deflect the suction pad 30 from position "A" to position "B", for example, generally defining a range of motion in a single plane. The deflection mechanism 70 can be manipulated to steer the suction pad 30 to a particular pericardial or epicardial site and to orient the suction cavity 50 to the pericardium or epicardium to form a respective pericardial or myocardial bleb.

The deflection mechanism can take any of the forms known in the medical device art. A commonly employed approach to providing controllable deflection of the distal end segments of catheters, guidewires, and stylets employs a generally straight outer sheath or tube and a pull or push or push-pull wire extending through a lumen of the outer sheath to an attachment point at the sheath distal end. The wire is pushed or pulled on at its proximal end typically through a handle that is permanently or removably attached to the catheter or guidewire proximal end. The proximal retraction or distal advancement of the pull or push wire, respectively, causes at least a distal segment of the outer sheath to bend or deflect. Examples of such deflection mechanisms in catheters can be found in U.S. Pat. Nos. 4,815,478, 4,898,577, 4,940,062, 5,545,200 and 6,251,092. U.S. Pat. Nos. 4,815,478 and 4,940,062 disclose the use of push-pull wires extending through guidewire lumens for deflecting a guidewire distal end by manipulating a handle at the guidewire proximal end.

Thus, deflection mechanism 70 can comprise a proximal handle at the suction tool proximal end assembly 14 coupled to a pair of pull wires extending from handle controls to opposite sides of the suction pad 30 to selectively induce bends in distal segment 72 to move the suction pad between positions "A" and "B" and intermediate positions therebetween.

In accordance with a further aspect of the invention, the suction pad distal end 60 is shaped to facilitate-advancement of the suction pad through the tissue incision to facilitate advancement of the suction pad 30 through and widening of the pericardial incision 114 as depicted in FIG. 8. For example, shaped suction pad distal ends 60', 60", and 60''' of respective suction pads 30', 30", 30''' are depicted in FIGS. 12A–12B, 13A–13B, and 14A–14B, respectively. The depicted "shovel" or "snout" shapes of suction pad distal ends 60', 60", and 60''' generally are shaped to provide a leading end or "leader" 74', 74", 74''' that can be easily inserted into the tissue incision, particularly the pericardial incision 114, followed by a "dilator" 76', 76", 76''' to widen the pericardial incision 114 as the respective suction pad 30', 30", 30''' is inserted through it. The leader 74' is a rounded tip, the leader 74" is a pointed tip, and the leader 74''' is ball-tip.

Returning to the cutting instrument, cutting blade 84 of FIGS. 1 and 7 can be shaped in a variety of ways, e.g., the exemplary blades 84', 84" and 84''' depicted in FIGS. 15–17 to facilitate making the tissue incision, particularly the pericardial incision 114 through the pericardium 106. Generally, like cutting blade 84, the cutting blades 84' and 84" incorporate a sharpened perforation tip 88' and 88" and trailing cutting blade edges 85' and 85". The cutting blade 84''' incorporates a blunt leading tip 88'''. Trailing cutting blade edges 85', 85" and 85''' make the tissue incision, through the tissue layer held against the convex upper wall 36 by suction. In this way, the pericardial incision 114 can be made through the pericardial bleb 136 maintained by suction in the suction cavity 50 as depicted in FIG. 7.

The cutting blade 84' of FIG. 15 comprises the sharpened perforation tip 88' and "V" shaped blade edge 85'. The pericardium 106 is punctured by the sharpened perforation tip 88' and is slitted as it is trapped in the "V" shaped blade edge 85' while the cutting blade 84' is advanced through the elongated suction cavity 50.

The cutting blade 84" of FIG. 16 comprises a sharpened leading blade point 85" and the elongated blade edge 85" that is inverted from the blade edge orientation shown in cutting blade 84. The cutting blade 84" is advanced through the tissue, e.g., the pericardium 106, to make a relatively limited tissue incision, e.g., a limited size pericardial incision 114.

The cutting blade 84''' of FIG. 17 can be used after such a limited tissue incision is made by use of a cutting instrument having a cutting blade 84'' of FIG. 16. The cutting blade 84''' comprises the blunt leading blade point 85''' and the trailing "V" shaped blade edge 85'''. The blunt leading blade point 85''' is advanced through the pericardial incision 114, and the pericardium is slitted as it is trapped in the "V" shaped blade edge 85''' while the cutting blade 84''' is advanced through the elongated suction cavity 50.

Figure 18:
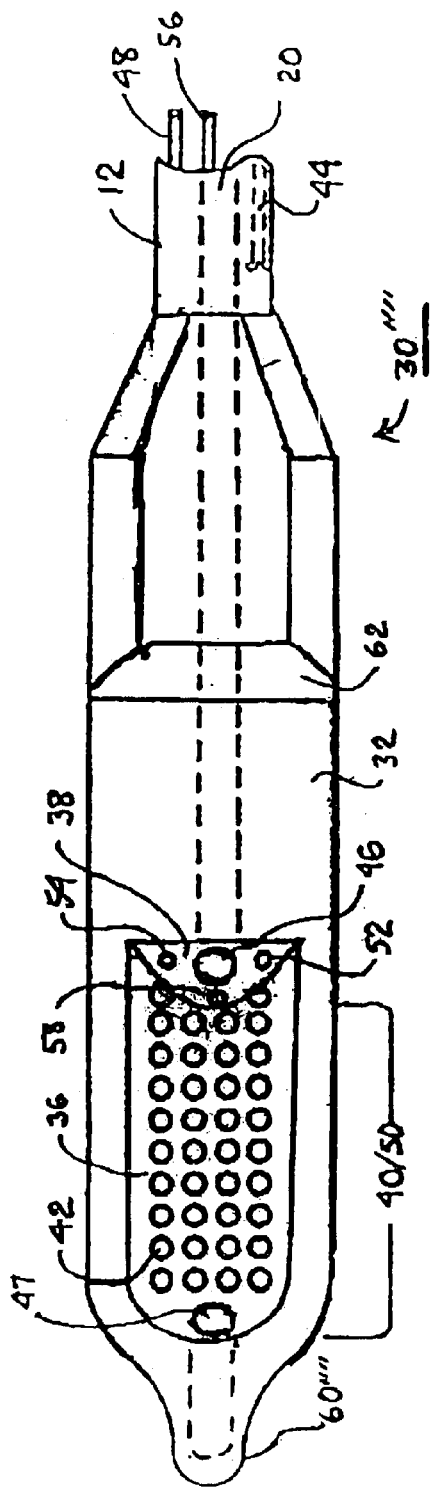
FIG. 18 is a plan view of a further variation of the distal suction pad of the suction tool of FIGS. 1–11.
Figure 19:
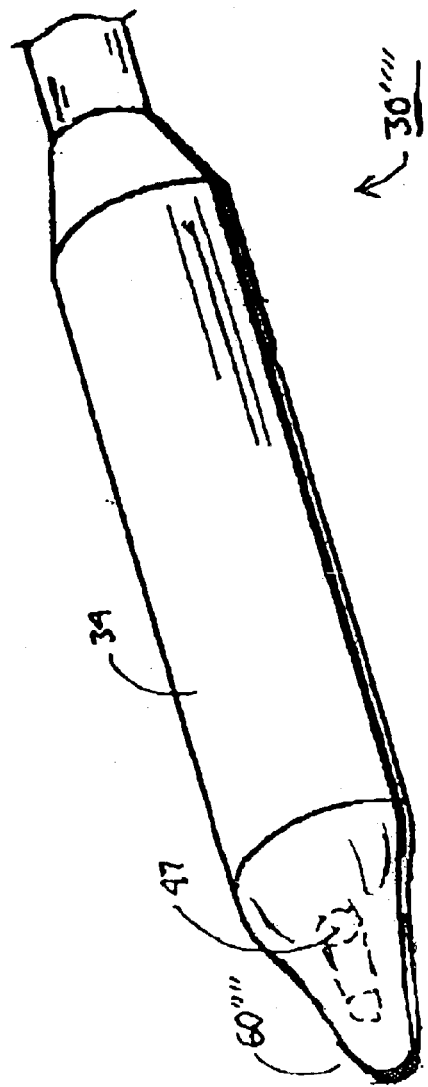
FIG. 19 is a perspective view of the distal suction pad of FIG. 18.

The suction tool 10 as described above can be further modified to facilitate making and increasing the length of such tissue incisions, e.g. pericardial incision 114, and to facilitate implantation of cardiac leads into or through the myocardial bleb 146. In particular, an elongated, tapered, suction pad distal end 60''' is depicted in the suction pad 30''' of FIGS. 18 and 19 enclosing a distally extending slot or recess 47. The distally extending slot or recess 47 is axially aligned with the working lumen 20 and the working lumen port 46 as shown in FIGS. 18 and 19. Thus, the cutting instrument 80 can be pushed distally so as to advance the cutting blades 84, 84', 84'', 84''' all the way across the tissue bleb, e.g., pericardial bleb 136 of FIG. 7, to lodge the cutting blade distal tip 88, 88', 88'', and 88''' within the recess 47. Then, the cutting tool can be withdrawn, and the suction pad 30'''' can be advanced into the pericardial space, steered to a desired site of the epicardium under visualization, and deployed against the epicardium, as described above. Suction can be applied to draw the myocardial bleb 146 into the suction cavity 50.

Referring to FIGS. 20–23, the distal slot or recess 47 of the modified suction pad 30'''' can also be used to facilitate deployment of particular cardiac leads having distal fixation mechanisms in the myocardial bleb 146 or distal to the myocardial bleb 146. After the myocardial bleb 146 is formed in suction cavity 50, the assembly of an exemplary cardiac lead 150 and cardiac lead installation tool 160 is inserted through the suction tool working lumen 20 and advanced through the myocardial bleb 146 as shown in FIG. 20. The cardiac lead distal fixation mechanism 154 (shown in FIG. 22) is restrained within or by the cardiac lead installation tool 160 during such advancement.

The installation tool 160 can comprise a catheter-like instrument having a installation tool lumen that the cardiac lead body and distal fixation mechanism is fitted into. The installation tool distal end 162 can comprise a conductive surface coupled through a conductor or a conductive tool shaft wall to the installation tool proximal end to be coupled with external test equipment to determine pacing and sensing thresholds.

The installation tool distal end 162 is preferably needle-shaped to pass through the myocardial bleb 146, in a path through a proximal perforation of the epicardium 140, the myocardium 142 and back through a distal perforation of the epicardium 140, and into the distal recess 47. In this way, the distal recess 47 receives the distal end 152 of the cardiac lead 150 and the distal end 162 of the cardiac lead installation tool 160 that is pushed through the myocardial bleb 146 to dispose the cardiac lead distal end 152 and the distal fixation mechanism 154 distal to the distal epicardial perforation. A cardiac electrode 158, e.g., a pace/sense electrode, is positioned to be disposed within the myocardial bleb 146 when the fixation tool is withdrawn over the cardiac lead 150 as depicted in FIG. 21.

The deployable distal fixation mechanism 154 at the cardiac lead distal end 152 restrained by the installation tool can thereby be advanced through the myocardial bleb 146 and into the distal recess 47. The lead installation tool 160 is manipulated, e.g., simply by retracting the installation tool distal end 162, to release the distal fixation mechanism 154 within the distal recess 47 and is then fully retracted over the cardiac lead 150, leaving the cardiac lead disposed as shown in FIG. 22.

The cardiac lead 150 can then be retracted sufficiently to release the distal fixation mechanism 154 from the distal recess 47 so that it bears against the epicardium 140 outside of the distal epicardial perforation as shown in FIG. 23. The distal fixation mechanism 154 preferably comprises one of a spiral that can be wound down to fit a lumen of the cardiac lead installation tool 160. One example of a screw-in lead is disclosed in U.S. Pat. No. 5,076,285 to Hess et al., incorporated herein by reference. The distal fixation mechanism 154 may comprise one or more elongated flexible, metal or silicon rubber or polyurethane pliant hooks, prongs or tines that can be flattened or otherwise aligned with and restrained within a lumen of the cardiac lead installation tool 160. One example of a tined lead is disclosed in U.S. Pat. No. 3,902,501 to Citron and Dickhudt, incorporated herein by reference. An exemplary three-tined fixation mechanism is depicted in FIGS. 22 and 23 that can be folded to fit into an installation tube lumen and that springs back into shape when released.

Suction is then interrupted allowing the suction tool 10 to be retracted over the cardiac lead 150. The myocardial bleb 146 flattens out, leaving the distal section of the lead body including the cardiac pace/sense electrode 158 within the myocardium 142 and extending out of the proximal and distal epicardial perforations 144 and 148. The flexible tined distal fixation mechanism 154 bears against the epicardium 140 to resist withdrawal of the cardiac pace/sense electrode 158 within the myocardium 142.

The suction tool 10 can be further modified to incorporate a pair of elongated electrodes attached to the suction pad lower wall extending alongside the suction cavity 50. In use, suction is applied to form the pericardial bleb 136, and ablation current can be applied to the electrodes that would create the peridardial incision 114. The electrodes can also be used when the suction pad 30 is applied to the epicardium 140 to conduct a mapping and threshold determination to locate optimal pace/sense sites for implantation of cardiac electrodes.

The tubular access sleeve 10 can be circular or oval or have any other desirable cross-section shape. The tubular access sleeve 10 can be straight, curved or formed with a bend or formed of a bendable material to be shaped by the user.

The access to the pericardial space in accordance with the present invention facilitates the performance of a number of ancillary procedures. For example, the procedures include introducing and locating the distal end of a catheter or guidewire or an electrode of a cardiac ablation catheter or a pacing lead or a cardioversion/defibrillation lead within the pericardial space and attached to the epicardium or myocardium. Other possible procedures include performing a coronary artery anastomosis in a thoracoscopic CABG procedure, replacing a defective heart valve, ablating aberrant electrical pathways in the atria to alleviate atrial tachyarrhythmias, introducing cells, drugs or anti-bacterial agents into the pericardial space, relieving pericardial fluid pressure or providing cardiac resynchronization therapy. Other procedures that can be performed in the pericardial space, include fluid withdrawal, drug delivery, cell delivery, diagnostic and therapeutic electrophysiology procedures, transmyocardial revascularization, transmyocardial revascularization with drug delivery, placement of the left ventricular assist devices, placement of the arterial bypass graphs, in situ bypass, i.e., coronary artery-venous fistulae, placement of drug delivery depots, closure of the left arterial appendage, and the like.

Figure 25:
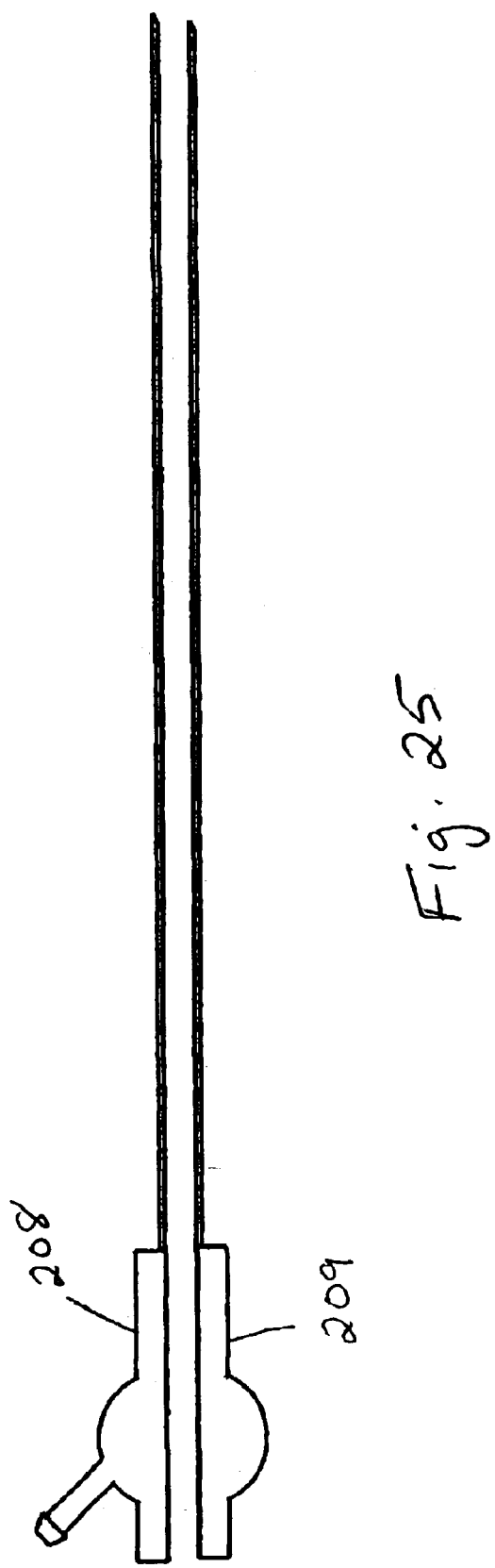
FIG. 25 is a schematic illustration of a split in half cardiac lead installation tool.

Referring to FIG. 24, cardiac lead installation tool 160 may comprise a catheter-like instrument, a hollow tube or needle 200. The hollow tube or needle 200 may be longitudinally splittable into two or more parts or halves (208 and 209), thereby allowing tube 200 to be easily removed from around an implanted cardiac lead (see FIG. 25). For example, a number of leads have connectors at their proximal ends having diameters considerably larger than the lead body. Therefore, if the inside diameter of tube 200 is only slightly larger in diameter than the cardiac lead body, the larger connector will not fit through the tube lumen. For this reason, it is preferable that tube 200 be splittable or slittable, thereby allowing tube 200 to be easily removed from a cardiac lead after implantation of the distal end of the cardiac lead into heart tissue. Tube 200 may be made of an appropriate material such as a biocompatible metal or plastic. A metal tube 200 may be made to be stiff as well as thin walled. A plastic tube 200 may be made to be flexible enough so that it may be inserted into working lumen 20 of a bent malleable suction tool body 12. In addition, the flexibility of a plastic tube 200 may allow a malleable suction tool body 12 to be bent while plastic tube 200 resides in working lumen 20 of suction tool body 12. Additionally, a plastic tube 200 may be slit open using a sharp instrument, for example, a razor-type device similar to slitting devices used in percutaneous lead delivery tools. In one embodiment of the invention, a plastic tube 200 may be slit off a lead using a slitting tool following implantation of the lead into the heart.

The proximal end of cardiac lead installation tool 160 may comprise a handle 210. Handle 210 may include one or more lumens or ports. For example, as shown in FIG. 24, handle 210 may comprise vacuum ports 220 and 225. Vacuum port 220 may include a hose fitting 221, as shown, for attachment to a vacuum supply hose. Vacuum port 225 may be used to couple to and transfer vacuum to suction lumen 44 of suction tool 10. Alternatively, vacuum port 225 may be configured to supply vacuum to working lumen 20 of suction tool 10. In this embodiment, suction is directed between the outer portion of inserted tube 200 and the inner portion of working lumen 20 and through the working lumen port 46 as well as the array of suction ports of suction tool 10.

Cardiac lead installation tool 160 includes a cardiac lead insertion port 230 and insertion lumen 240. Cardiac lead installation tool 160 may be sized to constrain a cardiac lead inserted into lumen 240 appropriately to allow twisting of the proximal end of the cardiac lead to be translated to the distal end of the cardiac lead, if so desired. In addition, the tube 200 may also be turned thereby twisting or turning the distal tip of a cardiac lead inserted into lumen 240. As mentioned earlier, the installation tool distal end 162 may comprise a sharpened or pointed tip, for example, a needle-like tip. The distal end 162 may be used to puncture the epicardium, thereby allowing the distal end of a cardiac lead to be placed or inserted into the myocardium through tube lumen 240. The installation tool distal end 162 may be used to puncture or penetrate just the epicardium, or it may be pushed farther into the myocardium to a desired lead implant depth.

Figure 26:
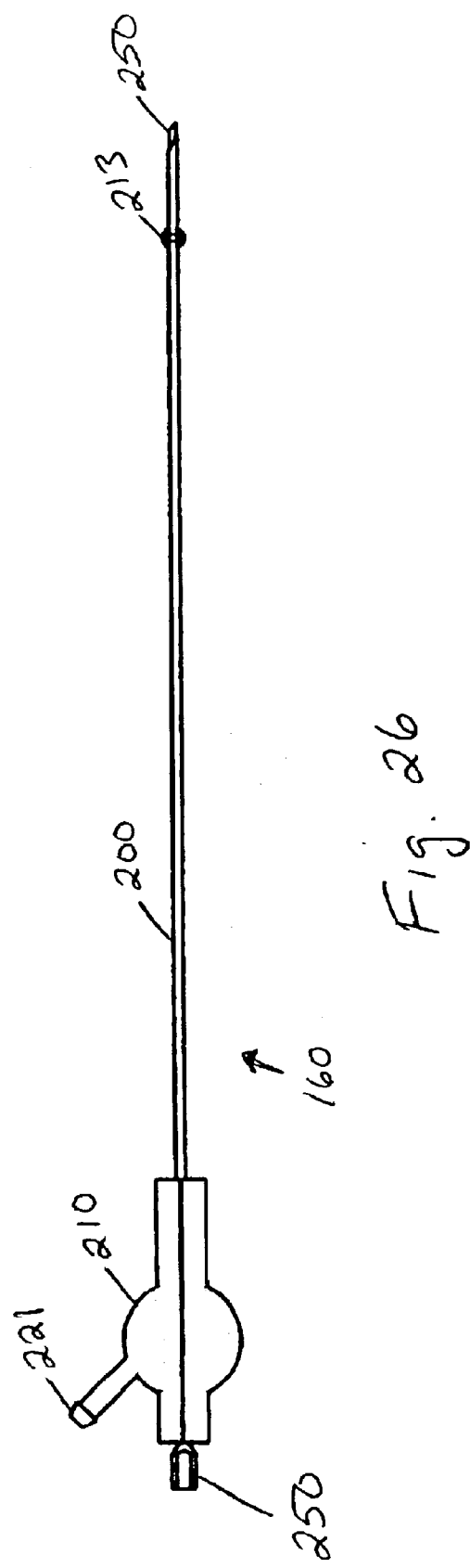
FIG. 26 is a schematic illustration of a cardiac lead installation tool.

Referring to FIG. 26, an appropriately sized needle, rod or trocar-like device 250 may be inserted into lumen 240 of cardiac lead installation tool 160. Preferably, a sharp tipped needle device 250 is used if the installation tool distal end 162 comprises a blunt end. In this embodiment of the invention, needle 250 inserted into tube lumen 240 may be used to create a puncture or hole in the epicardium. Following, puncturing of the epicardium, needle 250 may be removed from installation tool 160 followed by placement or insertion of a cardiac lead into tube lumen 240. The distal end of the cardiac lead may be pushed or inserted into the puncture or hole created in the epicardium by needle 250. The advantage of this embodiment is that the blunt distal end of tube 200 may be pushed into the myocardium to provide a blunt guide to the correct depth for placement of the distal end of a cardiac lead. Alternatively, needle 250 inserted into tube lumen 240 may be used create a small hole in the epicardium followed its removal and the insertion of a cardiac lead into tube lumen 240 until the distal end of the cardiac lead is pushed through the small hole in the epicardium and into the myocardium to a final destination depth. Alternatively, the distal end of the cardiac lead pushed through tube lumen 240 may puncture or create a hole in epicardium and/or myocardium. For example, a cardiac lead comprising a fixation screw at its distal end may be screwed into and through the epicardium and into the myocardium. The cardiac lead may be rotated an appropriate number of turns to fix it to the myocardium tissue. Collar 213 is used to center tube 200 within working lumen 20 of suction tool 10. Collar 213 may also be designed to be splittable or slittable.

Figure 27:
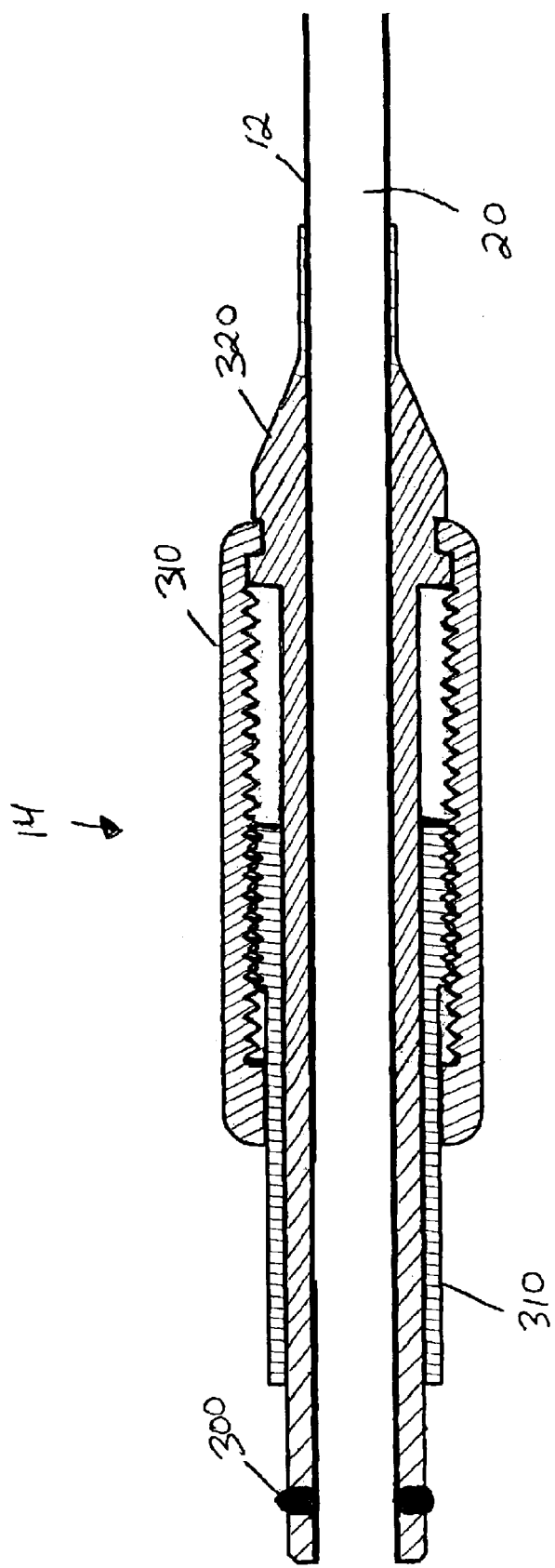
FIG. 27 is a schematic illustration of a portion of a suction tool.
Figure 28:
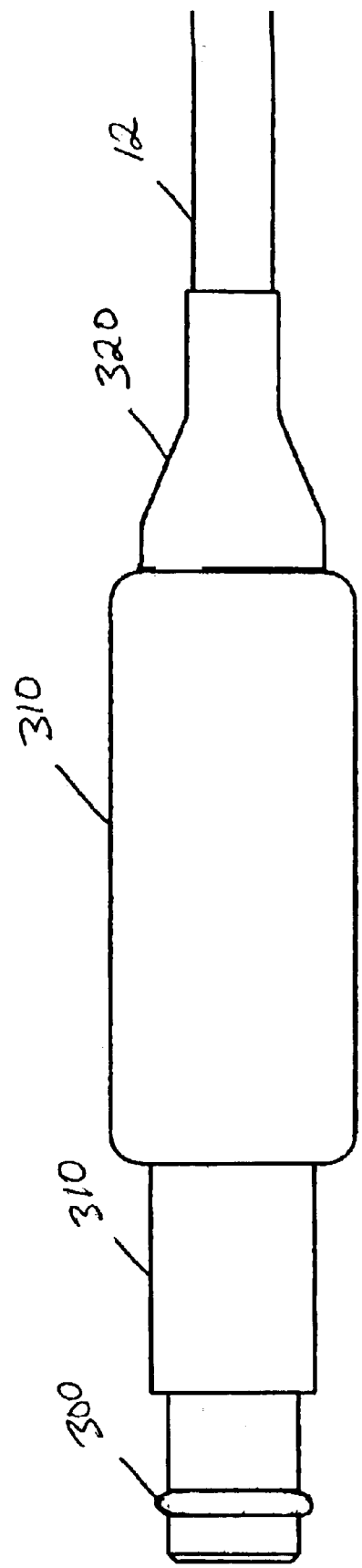
FIG. 28 is a schematic illustration of a portion of a suction tool.

Referring to FIGS. 27 and 28, one embodiment of suction tool 10 includes an adjustable suction tool proximal end assembly 14 mounted at the proximal end of suction tool body 12. The suction tool proximal end assembly 14 comprises the proximal end opening of the suction tool working lumen 20, a vacuum seal O-ring 300, a threaded collar 310, a collar mounting component 320, and a threaded tool stop 330. Collar mounting component 320 is rigidly coupled to suction tool body 12 and is designed to hold collar 310 in place while allowing collar 310 to be rotated freely about suction tool body 12. Rotation of collar 310 causes tool stop 330, a portion of which is threaded inside collar 310, to move proximal or distal relative to suction tool body 12. This adjustable "depth" control feature allows a surgeon to finely adjust the amount the distal end of a medical instrument or device, e.g., installation tool 160, inserted into working lumen 20, to advance out of the working lumen port 46. For example, a surgeon can "dial in" a pre-selected amount the distal end of installation tool 160 will protrude from working-lumen port 46. The surgeon can then remove and/or retract installation tool 160 from port 46. Suction tool 10 may then be manipulated thereby positioning suction pad 30 at a desired tissue site. Installation tool 160 can then be advanced or inserted back into working lumen 20 until handle 210 of installation tool 160 engages tool stop 330 thereby pre-selecting the distance the distal end of installation tool 160 protrudes from working lumen port 46. This distance may be, for example, from about 0 to about 5 cm. This adjustable "depth" control feature can allow a surgeon to accommodate patients, for example, with diseased epicardial tissue but more viable myocardial and/or endocardial tissue. For example, if the pacing threshold achieved at a more superficial lead placement depth is not desirable, the depth can be changed so that the lead is placed deeper into tissue. At this deeper location the pacing threshold may be more advantageous.

Figure 29:
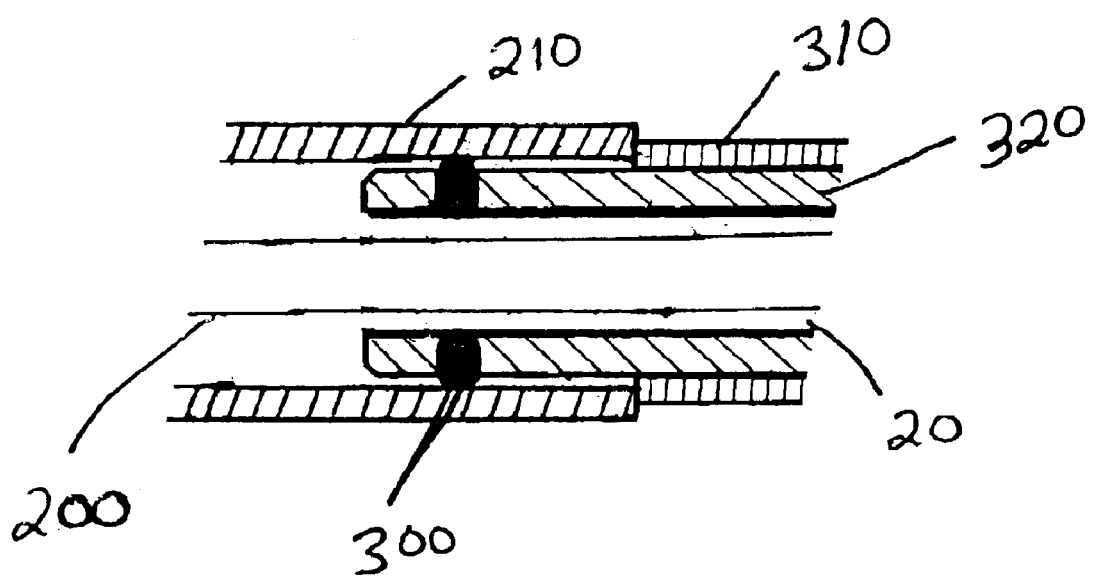
FIG. 29 is a schematic illustration of a portion of a suction tool and a cardiac lead installation tool.

In one embodiment of the invention, tube 200 of installation tool 160 is inserted into working lumen 20 of suction tool 10 until handle 210 of installation tool 160 engages collar mounting component 320 and tool stop 330, both of suction tool 10. Vacuum seal O-ring 300 of suction tool 10 engages handle 210 of installation tool 160, thereby creating a fluid connection between vacuum port 225 of installation tool 160 and working lumen 20 and/or suction lumen 44 of suction tool 10, thereby allowing suction to be communicated from vacuum port 220 of installation tool 160 to working lumen port 46 and/or suction ports 42 of suction tool 10 (see FIG. 29).

Figure 30:
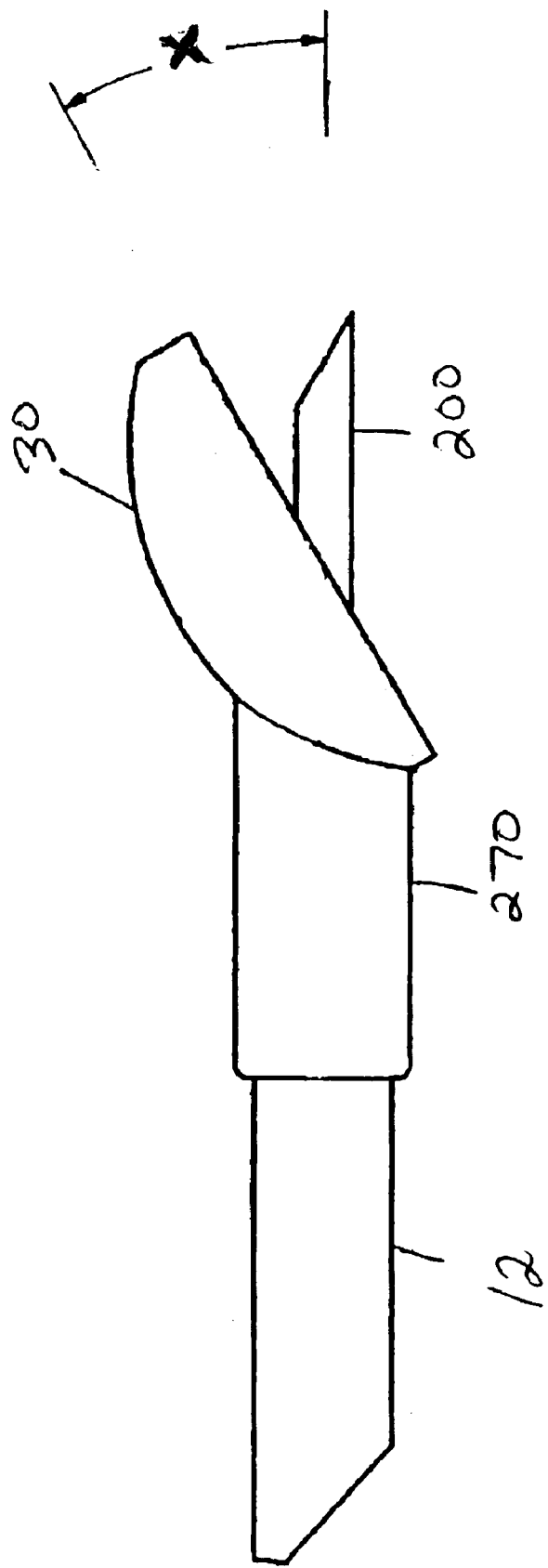
FIG. 30 is a schematic illustration of a portion of a suction tool.
Figure 31:
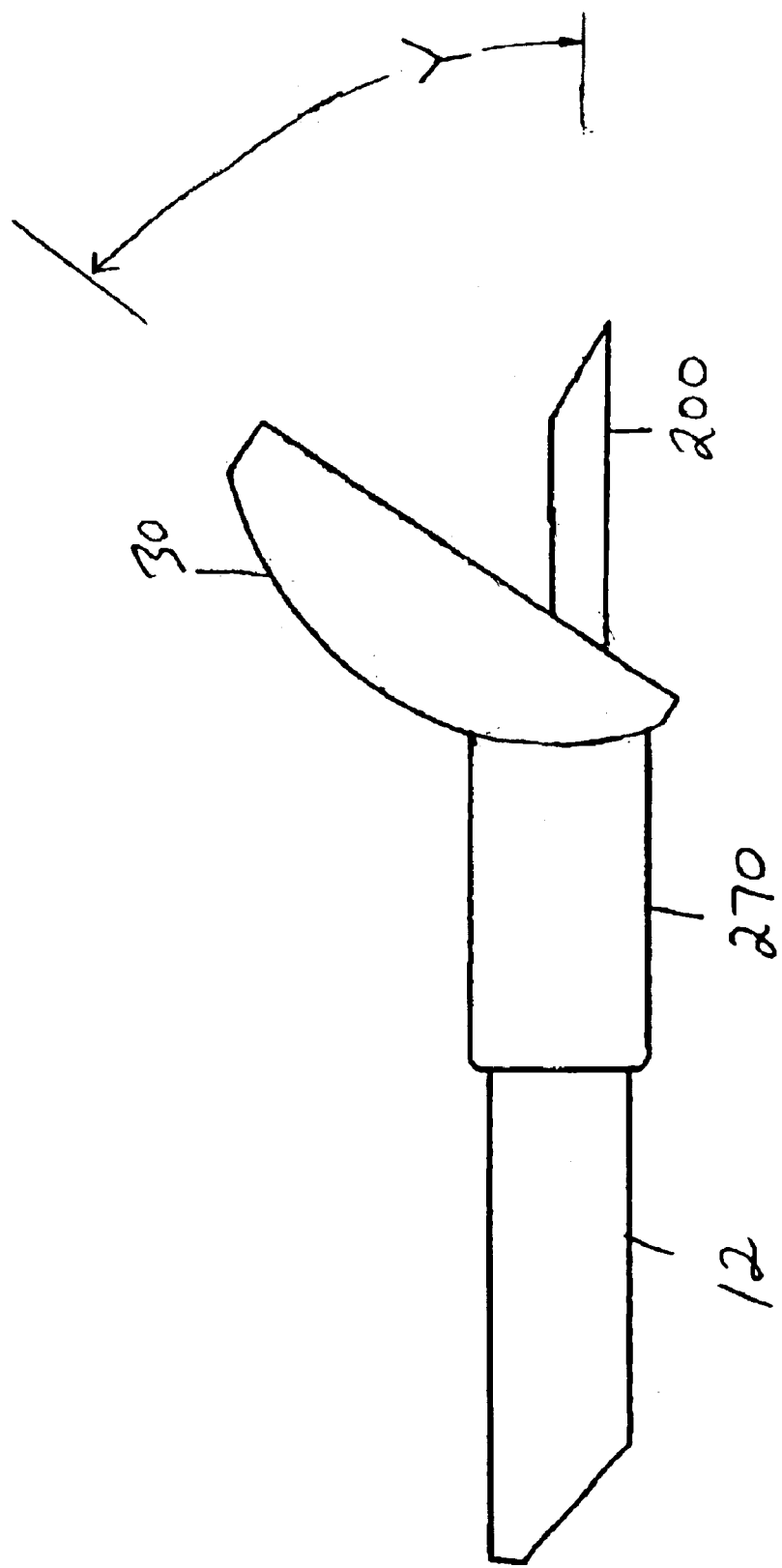
FIG. 31 is a schematic illustration of a portion of a suction tool.

Referring to FIGS. 30 and 31, suction tool 10 may be equipped with a deflection mechanism 270 that a surgeon can manipulate at the suction tool proximal end assembly 14 to change the angle between suction pad 30 and suction tool body 12. A deflection mechanism 270 may be incorporated into suction tool body 12 or suction pad 30. Deflection mechanism 270 may be used to deflect suction pad 30 from an angle "X" to an angle "Y", for example, generally defining a range of motion in a single plane. The deflection mechanism 270 may be manipulated to change the angle of entry of a distal end of a tool advanced through working lumen 20 of suction tool 10 into tissue engaged by suction pad 30. For example, the larger the angle, e.g., angle Y, between suction pad 30 and suction tool body 12, the more perpendicular the distal end of installation tool 160 will penetrate tissue when advanced out of the working lumen port 46, whereas the smaller the angle, e.g., angle X, between suction pad 30 and suction tool body 12, the more tangential the distal end of installation tool 160 will penetrate tissue when advanced out of the working lumen port 46. Therefore, deflection mechanism 270 can allow a surgeon to select an appropriate angle of penetration of a tool advance out of working lumen port 46 into tissue engaged by suction pad 30.

The deflection mechanism 270 can take any of the forms known in the medical device art. A commonly employed approach to providing controllable deflection of the distal end segments of catheters, guidewires, and stylets employs a generally straight outer sheath or tube and a pull or push or push-pull wire extending through a lumen of the outer sheath to an attachment point at the sheath distal end. The wire is pushed or pulled on at its proximal end typically through a handle that is permanently or removably attached to the catheter or guidewire proximal end. The proximal retraction or distal advancement of the pull or push wire, respectively, causes at least a distal segment of the outer sheath to bend or deflect. Examples of such deflection mechanisms in catheters can be found in U.S. Pat. Nos. 4,815,478, 4,898,577, 4,940,062, 5,545,200 and 6,251,092. U.S. Pat. Nos. 4,815,478 and 4,940,062 disclose the use of push-pull wires extending through guidewire lumens for deflecting a guidewire distal end by manipulating a handle at the guidewire proximal end. Thus, deflection mechanism 270 can comprise a proximal handle at the suction tool proximal end assembly 14 coupled to a pair of pull wires extending from handle-controls to suction pad 30 to selectively move suction pad 30 relative to working lumen 20 of suction tool body 12 between angle positions 0 degrees and 90 degrees and positions therebetween, e.g., "X" and "Y".

Deflection mechanism 270 can allow suction tool 10 to accommodate a variety of approach procedures including sternotomy, thoracotomy, and thoracoscopy procedures. For example, depending on the angle of approach the surgeon is taking relative to a targeted tissue site and depending on the particular procedure, e.g., lead delivery, ablation and/or cell delivery, the more or less angle the surgeon may want suction pad 30 to be relative to working lumen 20. It may be desirable to have a lead implanted tangentially to the surface of heart to reduce the strain at the surface of the heart on the lead. In the case of a cell delivery procedure, it may be more desirable to implant the cells more perpendicular to the surface of the tissue or organ thereby placing the cells more deeply into the targeted tissue.

An alternative embodiment of the present invention is to fix the angle between suction pad 30 and working lumen 20. In a preferred embodiment, this angle is fixed at approximately 30 degrees. In cases where the angle needs to be approximately 0 degrees, suction pad 30 may be made to include a channel, slot or groove within the suction pad 30 thereby allowing a cardiac lead to be directed out of suction pad 30 at an angle greater than 0 degrees, preferably 30 degrees relative to the surface of the heart.

Figure 32:
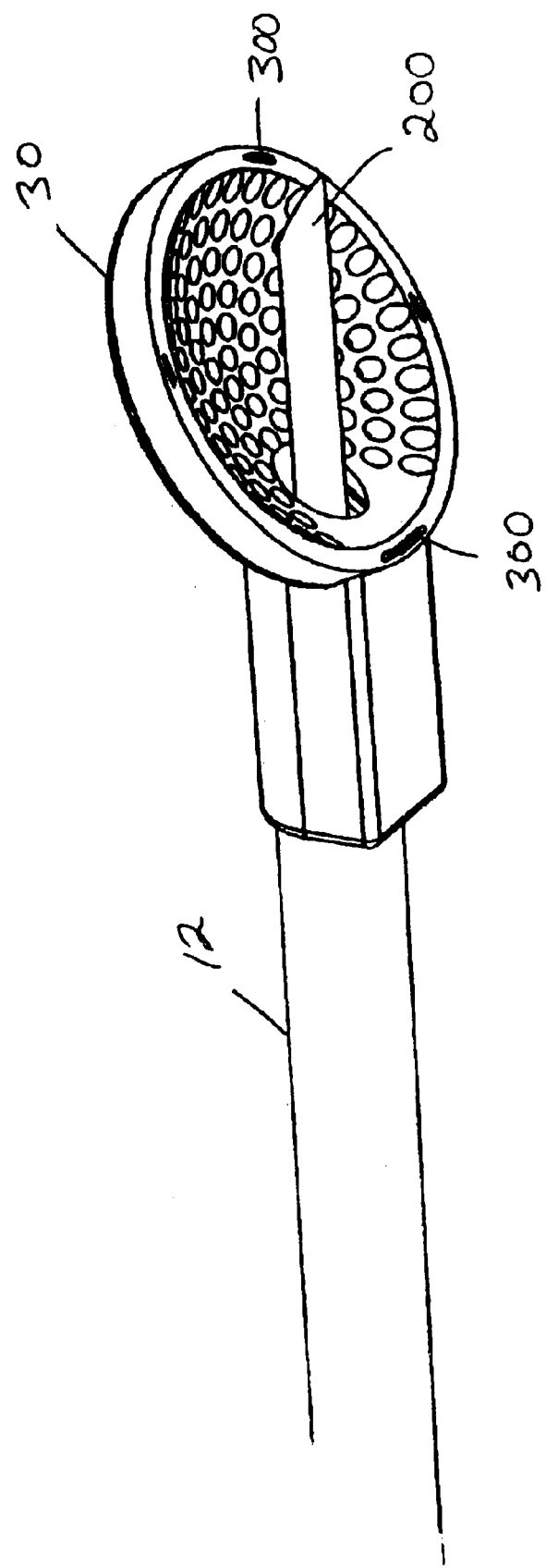
FIG. 32 is a schematic illustration of a portion of a suction tool and a cardiac lead installation tool.

Referring to FIG. 32, suction tool 10 may be modified to incorporate one or more sensors 300 for sensing or monitoring, e.g., temperature, vibration, voltage, amperage, wattage and/or impedance. A vibration sensor may be used to sense the vibration in tissue that occurs prior to a "steam pop." Water (from within and around the tissue) present at an ablation site may be heated to exceed 100° C., if this happens, the water will change phase, boil and may result in an audible "steam pop" within the tissue. This pop may damage and even rupture the tissue. Irrigation cooling of the site shifts the location of the "steam pop" even deeper within the tissue, resulting in even greater damage than a superficial pop. It has been observed that before a "steam pop", there is a mechanical vibration within the tissue (suspected to be caused by the phase transition of water, which may create microbubbles within the tissue).

Alternatively, the one or more sensors of suction tool 10 may be any suitable blood gas sensor for measuring the concentration or saturation of a gas in the blood stream. For example, a sensor for measuring the concentration or saturation of oxygen or carbon dioxide in the blood and/or tissues may be employed.

Alternatively, the one or more sensors of suction tool 10 may be any suitable sensor for measuring blood pressure or flow, for example a Doppler ultrasound sensor system, or a sensor for measuring hematocrit (HCT) levels.

Alternatively, the one or more sensors of suction tool 10 may be a biosensor, for example, comprising an immobilized biocatalyst, enzyme, immunoglobulin, bacterial, mammalian or plant tissue, cell and/or subcellular fraction of a cell. For example, the tip of a biosensor may comprise a mitochondrial fraction of a cell, thereby providing the sensor with a specific biocatalytic activity.

Alternatively, the one or more sensors of suction tool 10 may be based on potentiometric technology or fiber optic technology. For example, the sensor may comprise a potentiometric or fiber optic transducer. An optical sensor may be based on either an absorbance or fluorescence measurement and may include an UV, a visible or an IR light source.

The one or more sensors of suction tool 10 may be used to detect naturally detectable properties representative of one or more characteristics, e.g., chemical, physical or physiological, of a patient's bodily tissues or fluids. For example, naturally detectable properties of patient's bodily tissues or fluids may include pH, fluid flow, electrical current, impedance, temperature, pressure, components of metabolic processes, chemical concentrations, for example, the absence or presence of specific peptides, proteins, enzymes, gases, ions, etc.

The one or more sensors of suction tool 10 may include one or more imaging systems, camera systems operating in UV, visible, or IR range; electrical sensors; voltage sensors; current sensors; piezoelectric sensors; electromagnetic interference (EMI) sensors; photographic plates, polymer-metal sensors; charge-coupled devices (CCDs); photo diode arrays; chemical sensors, electrochemical sensors; pressure sensors, vibration sensors, sound wave sensors; magnetic sensors; UV light sensors; visible light sensors; IR light sensors; radiation sensors; flow sensors; temperature sensors; or any other appropriate or suitable sensor. The one or more sensors of suction tool 10 may be powered by any suitable power source. In addition, the one or more sensors of suction tool 10 may be coupled to any appropriate output device, for example, a LCD or CRT monitor which receives and displays information regarding the one or more sensors.

A temperature sensor may incorporate one or more temperature-sensing elements such as, for example, thermocouples, thermisters, temperature-sensing liquid crystals, or temperature-sensing chemicals. A temperature sensor could be used, for example, to monitor tissue temperature generated by an ablation apparatus.

Ablation may be performed by heating the tissue to a suitable temperature. Alternatively, ablation may be performed by freezing the tissue to a suitable temperature. The change in tissue temperature may be sensed and/or monitored by one or more temperature sensors of suction tool 10. In one embodiment, the change in tissue temperature may be displayed on an output device. By software control, the user may choose to display the information in a number of ways. The output device may show the current temperature of each sensor. The output device may also lock and display the maximum temperature achieved at each sensor. The output device may also indicate when each sensor has reached an appropriate combination of temperature and time to ensure cell/tissue death.

The signals from one or more sensor may preferably be amplified by a suitable amplifier before reaching an output device. The amplifier may also be incorporated into an output device. Alternatively, the amplifier may be a separate device. The output device may incorporate one or more processors.

In one embodiment, a plurality of temperature sensors may be positioned around the perimeter of suction pad 30. When sensed tissue reaches a certain temperature, the corresponding temperature sensor may send a signal. Preferably, the temperature sensor may send constant signals. For example, thermocouples may send a constant signal based on their voltage. As the temperature changes, the voltage of the thermocouples may change proportionately and the signal sent by the thermocouples may change proportionately.

Figure 33:
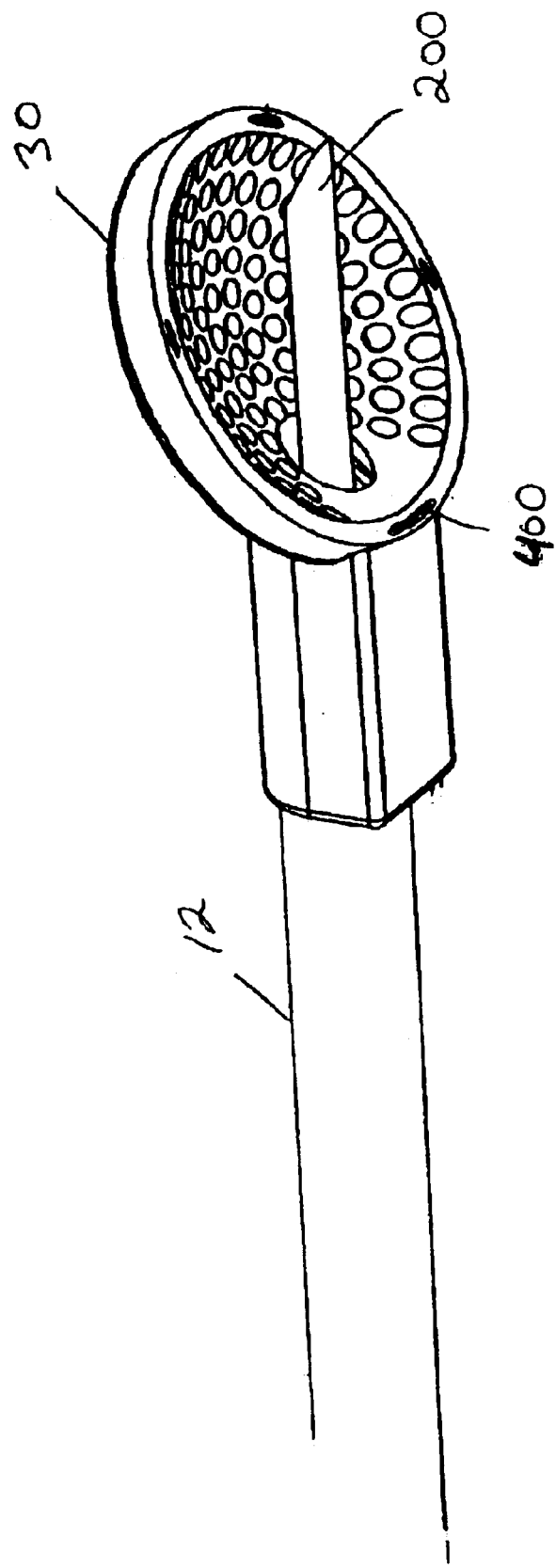
FIG. 33 is a schematic illustration of a portion of a suction tool and a cardiac lead installation tool.
Figure 34:
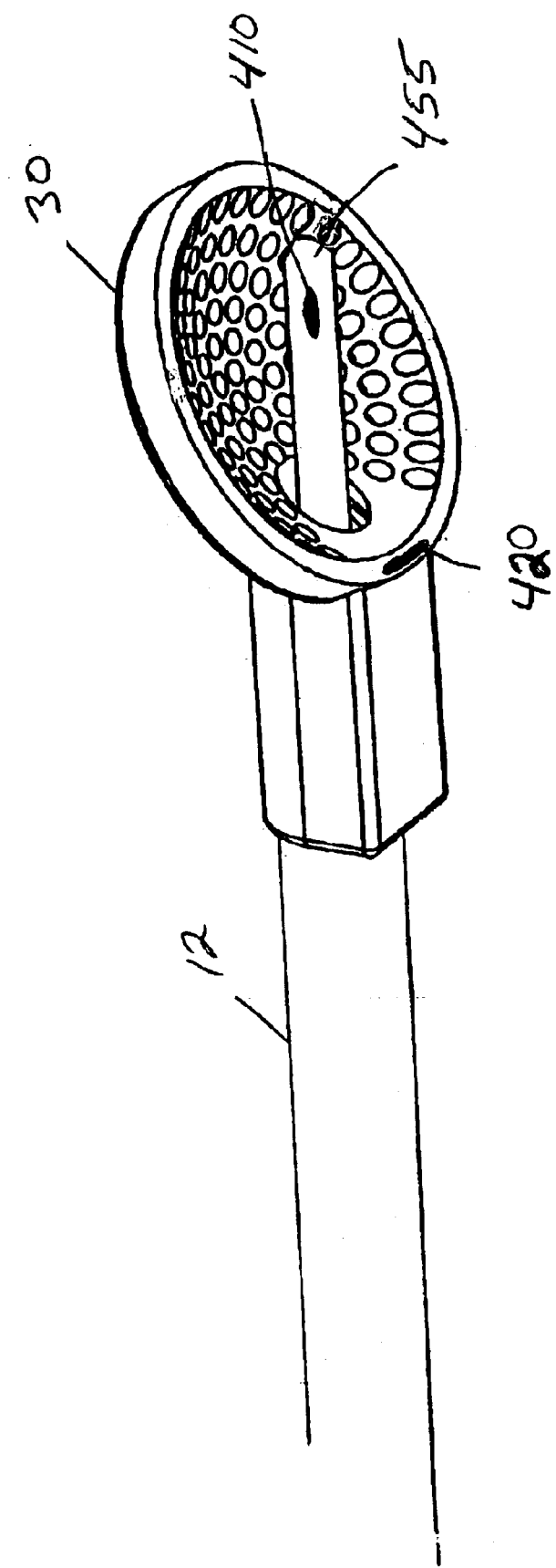
FIG. 34 is a schematic illustration of a portion of a suction tool and an ablation tool.

In one embodiment, suction tool 10 may comprise one or more energy transfer elements 400 positioned on, along, within or adjacent a tissue contact surface of suction tool 10 (see FIG. 33). Energy transfer elements may transfer tissue ablation energy to target tissue. For example, energy transfer elements may be conductive elements which may supply RF energy, microwave energy or ultrasound energy to target tissue. Energy transfer elements may be, for example, laser elements for supplying laser light to target tissue or they may be cryo elements for cooling target tissue. Two or more energy transfer elements or conductive elements of suction tool 10 may be arranged in a biopolar arrangement, for example one element may be used as a positive electrode and one element may be used as a negative electrode. One or more energy transfer elements or conductive elements of suction tool 10 may be arranged in a monopolar arrangement, for example, one element may be used as one electrode and an indifferent element-or electrode is placed elsewhere on the patient's body such as the back, thigh or shoulder or another site other than the suction tool site. Alternatively, one or more energy transfer elements, e.g., an electrode 420, of suction tool 10 may be used in combination with one or more energy transfer elements, e.g., an electrode 410, of an ablation tool 455 advanced through working lumen 20 and out working lumen port 46 (see FIG. 34). Suction tool 10 may include an indifferent (or non-ablating) electrode which may serve as the return plate for energy transmitted through an ablation tool advanced through working lumen 20 and out port 46 of suction tool 10. The ablation tool may be any suitable ablation tool such as, for example, a catheter, an electrocautery device, an electrosurgical device or an ablation wire having one or more energy transfer elements. Ablation tool and its components are preferably made of a biocompatible material such as stainless steel, biocompatible epoxy or biocompatible plastic.

Energy transfer elements or conductive elements may comprise one or more conductive materials or blends including titanium, titanium alloys, TiNi alloys, shape memory alloys, super elastic alloys, aluminum oxide, platinum, platinum alloys, stainless steels, stainless steel alloys, MP35N, elgiloy, haynes 25, stellite, pyrolytic carbon, silver carbon, conductive polymers or plastics, or conductive ceramics. Energy transfer elements or conductive elements may not be conductive but may serve as a conduit to deliver a conductive material such as a conductive fluid. Energy transfer elements or conductive elements may be porous. For example, energy transfer elements or conductive elements may comprise porous polymers, metals, or ceramics. Energy transfer elements or conductive elements may be coated with non-stick coatings such as PTFE or other types of coatings as discussed herein. Energy transfer elements or conductive elements may be flexible thereby allowing them to conform to the surface of target tissue. Energy transfer elements or conductive elements may be malleable thereby allowing a surgeon to shape them to conform to the surface of target tissue.

Energy transfer elements or conductive elements may comprise one or more metal conductors such as windings inside a polymer or a conductive mesh material. The energy transfer elements or conductive elements may comprise tubes for delivering fluids. The tubes may comprise holes or slots. A polymer tube may be placed inside a metal tube to control fluid deliver through energy transfer elements or conductive elements. One or more of the energy transfer elements or conductive elements may be used as stimulation electrodes, for example, nerve stimulation electrodes or cardiac stimulation electrodes.

Energy transfer elements or conductive elements may comprise needles designed to penetrate tissues such as fat and muscle. For example, energy transfer elements or conductive elements may be designed to penetrate fat on the heart thereby allowing the energy transfer elements or conductive elements to reach cardiac tissue. The needles may allow fluids such as conductive fluids, tissue ablation chemicals, drugs, and/or cells to pass through.

Figure 35:
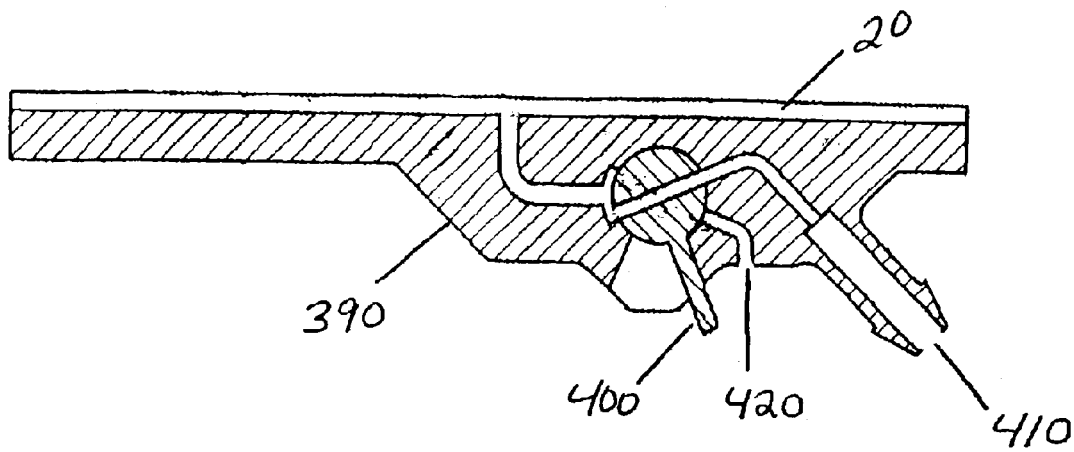
FIG. 35 is a schematic illustration of a portion of a suction tool.
Figure 36:
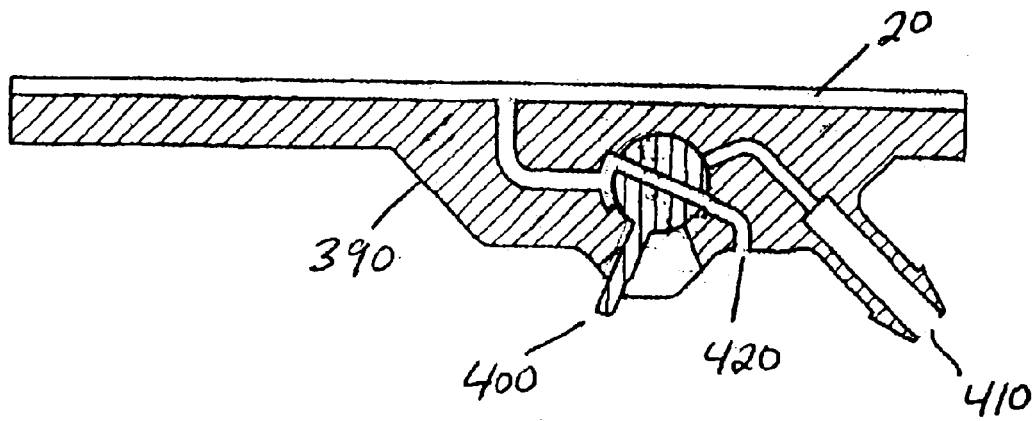
FIG. 36 is a schematic illustration of a portion of a suction tool.

Suction tool 10 may comprise one or more surgeon-controlled switches and/or valves. For example, a switch or valve may be incorporated in or on suction tool 10 or any other location easily and quickly accessed by the surgeon for regulation of suction device 10 by the surgeon. The switch or valve may be, for example, a hand switch or valve, a foot switch or valve, or a voice-activated switch or valve comprising voice-recognition technologies. For example, a vacuum valve may incorporated into a proximal handle 390 at the suction tool proximal end assembly 14 for controlling the application of suction to suction pad 30 (see FIGS. 35 and 36). As shown in FIG. 35, valve 400 may be manipulated by a surgeon to provide suction from suction port 410 thereby providing suction to working lumen 20 of suction tool 10. Alternatively, suction may be provided to suction lumen 44 of suction tool 10. As shown in FIG. 36, valve 400 may be manipulated by a surgeon to release suction from suction pad 30 and working lumen 20 and/or suction lumen 44 by venting to vent port 420. In one embodiment of suction tool 10, a switch for controlling the delivery of energy, e.g., from an RF generator, to one or more energy transfer elements may be incorporated into suction tool proximal end assembly 14. In one embodiment of suction tool 10, a switch for controlling one or more sensors may be incorporated into suction tool proximal end assembly 14. A visual and/or audible signal used to alert a surgeon to the completion or resumption of a medical procedure, for example, an ablation procedure, may be incorporated into suction tool 10. For example, a beeping tone or flashing light that increases in frequency as the medical procedure, e.g., an ablation procedure or cell delivery procedure, ends or begins may be used.

During a tissue ablation procedure, it is sometimes desirable to irrigate the ablation site with irrigation fluid, which may be, for example, any suitable fluid such as saline or another conductive fluid. The irrigating fluid may cool one or more energy transfer elements of suction tool 10 and may allow for greater lesion depth. Furthermore, continuous fluid flow may keep the temperature below the threshold for blood coagulation, which may clog suction tool 10 or an ablation device placed within suction tool 10. Use of irrigating fluid may therefore reduce the need to remove a clogged ablation device for cleaning or replacement. The presence of an ionic fluid layer between an energy transfer element and the tissue to be ablated may also ensure that an ionic fluid layer conforming to the tissue contours is created. In one preferred embodiment, saline solution is used. Alternatively, other energy-conducting liquids, such as Ringer's solution, ionic contrast, or even blood, may be used. Diagnostic or therapeutic agents, such as lidocaine, $CA^{++}$ blockers, ionic contrast, or gene therapy agents may also be delivered before, with or after the delivery of the irrigating fluid. A standard fluid pump, for example, may be used to deliver fluids. The pump may be connected to central power source or may have its own source of power. Suction tool 10 may include a means for delivering fluid to an ablation site from a fluid source. Such means may be, for example, fluid openings coupled to one or more fluid conduits or lumens.

A fluid source may be any suitable source of fluid. An fluid source may include a manual or electric pump, an infusion pump, a syringe pump, a syringe, a pressurized reservoir or bag, a squeeze bulb or other fluid moving means, device or system. For example, a pump may be connected to power source or it may have its own source of power. A fluid source may be powered by AC current, DC current, or it may be battery powered either by a disposable or re-chargeable battery. A fluid source may comprise one or more fluid regulators, e.g., to control fluid flow rate, valves, fluid reservoirs, conduits, lines, tubes and/or hoses. The conduits, lines, tubes, or hoses may be flexible or rigid. For example, a flexible line may be used to communicate fluid to suction tool 10, thereby allowing suction tool 10 to be easily manipulated by a surgeon. Fluid reservoirs, for example, may be an IV bag or bottle. It may be preferred that the fluid be sterile.

A fluid source may be incorporated into suction tool 10, thereby delivering fluid at targeted site. A fluid source may be slaved to suction tool 10, for example, to one or more sensors of suction tool 10. A fluid source may be designed to automatically stop or start the delivery of fluid during a medical procedure. A fluid source and/or suction tool 10 may be slaved to a robotic system or a robotic system may be slaved to a fluid source and/or suction tool 10.

Fluid from a fluid source may include saline, e.g., normal, hypotonic or hypertonic saline, Ringer's solution, ionic contrast, blood, or other energy-conducting liquids. An ionic fluid may be used electrically couple one or more electrodes of a suction tool 10 to the tissue to be ablated thereby lowering the impedance at the ablation site. An ionic fluid may create a larger effective electrode surface. A fluid may be used to cool the surface of the tissue thereby preventing the over heating or cooking of tissue which can cause popping, desiccation, and charring of tissue. A hypotonic fluid may be used to electrically insulate a region of tissue thereby preventing ablation of tissue by an electrical means.

Tissue and/or bodily fluids contacting components of suction tool 10 are preferably made of one or more biocompatible materials. Biocompatible materials or biomaterials are usually designed and constructed to be placed in or onto tissue of a patient's body or to contact fluid of a patient's body. Ideally, a biomaterial will not induce undesirable reactions in the body such as blood clotting, tumor formation, allergic reaction, foreign body reaction (rejection) or inflammatory reaction; will have the physical properties such as strength, elasticity, permeability and flexibility required to function for the intended purpose; may be purified, fabricated and sterilized easily; will substantially maintain its physical properties and function during the time that it remains in contact with tissues or fluids of the body.

Materials that are either biocompatible or may be modified to be biocompatible and may be used to make suction tool 10 and/or one or more of its components may include metals such as titanium, titanium alloys, TiNi alloys, shape memory alloys, super elastic alloys, aluminum oxide, platinum, platinum alloys, stainless steels, stainless steel alloys, MP35N, elgiloy, haynes 25, stellite, pyrolytic carbon, silver carbon, glassy carbon, polymers or plastics such as polyamides, polycarbonates, polyethers, polyesters, polyolefins including polyethylenes or polypropylenes, polystyrenes, polyurethanes, polyvinylchlorides, polyvinylpyrrolidones, silicone elastomers, fluoropolymers, polyacrylates, polyisoprenes, polytetrafluoroethylenes, rubber, minerals or ceramics such as hydroxapatite, epoxies, human or animal protein or tissue such as bone, skin, teeth, collagen, laminin, elastin or fibrin, organic materials such as wood, cellulose, or compressed carbon, and other materials such as glass, and the like. Materials that are not considered biocompatible may be modified to become biocompatible by a number of methods well known in the art. For example, coating a material with a biocompatible coating may enhance the biocompatibility of that material.

One or more surfaces of suction tool 10 and/or one or more of its components may be coated with one or more radioactive materials and/or biological agents such as, for example, an anticoagulant agent, an antithrombotic agent, a clotting agent, a platelet agent, an anti-inflammatory agent, an antibody, an antigen, an immunoglobulin, a defense agent, an enzyme, a hormone, a growth factor, a neurotransmitter, a cytokine, a blood agent, a regulatory agent, a transport agent, a fibrous agent, a protein, a peptide, a proteoglycan, a toxin, an antibiotic agent, an antibacterial agent, an antimicrobial agent, a bacterial agent or component, hyaluronic acid, a polysaccharide, a carbohydrate, a fatty acid, a catalyst, a drug, a vitamin, a DNA segment, a RNA segment, a nucleic acid, a lectin, an antiviral agent, a viral agent or component, a genetic agent, a ligand and a dye (which acts as a biological ligand). Biological agents may be found in nature (naturally occurring) or may be chemically synthesized by a variety of methods well known in the art.

Suction may be provided by the standard suction available in the operating room. The suction source may be coupled to suction tool 10 with a buffer flask. Alternatively, suction, may be provided via a manual or electric pump, a syringe, a suction or squeeze bulb or other suction or vacuum producing means, device or system. The suction source may comprise one or more vacuum regulators, valves, e.g., vacuum releasing valves, conduits, lines, tubes and/or hoses. The conduits, lines, tubes, or hoses may be flexible or rigid. For example, a flexible suction line may be used to communicate suction to suction tool 10, thereby allowing suction tool 10 to be easily manipulated by a surgeon. Another method that would allow the surgeon to easily manipulate suction tool 10 includes incorporation of a suction source into suction tool 10. For example, a small battery operated vacuum pump may be incorporated into suction tool 10. A suction source may include a visual and/or audible signal used to alert a surgeon to any change in suction. For example, a beeping tone or flashing light may be used to alert the surgeon when suction is present.

One or more portions of suction tool 10 may be malleable, flexible, bendable and/or moveable. For example, suction tool 10 may comprise one or more hinges or joints (not shown) for maneuvering and placing suction pad 30 against tissue. The hinges or joints of suction tool 10 may be actuated, for example, from handle located at the proximal suction tool port assembly 14. Suction tool body 12 may be malleable or shapeable. One or more hinges or joints may be used to move suction pad 30 relative to suction tool body 12 and/or working lumen 20.

An output device (not shown) coupled to suction tool 10 may be used to control, for example, a suction source, a power source or generator, a cell delivery source, and/or a fluid delivery source. For example, a signal of a first intensity from a sensor of suction tool 10 may indicate that the power level from a power source should be lowered; a signal of a different intensity may indicate that the power source should be turned off. Preferably, an output device may be configured so that it may automatically raise or lower the power from a power source appropriately. Alternatively, the control of a power source, for example, based on output from output device may be manual.

An output device coupled to suction tool 10 may also be a visual display that indicates to the user the status of a medical procedure. Such a display may be, for example, an indicator on a LCD or CRT monitor. By software control, the surgeon may choose to display the information in a number of ways. The monitor may show the current reading of each sensor, for example. The monitor may also lock and display the maximum reading achieved at each sensor. For example, a monitor may indicate when an appropriate combination of temperature and time has been reached to ensure cell death during an ablation procedure. One such appropriate combination may be 60° C. for 5 seconds. Another combination may be 55° C. for 20 seconds. Information may be displayed to the user in any other suitable manner, such as for example, displaying a virtual representation of an ablation lesion on the monitor.

Alternatively, the monitor may display the voltage corresponding to the signal emitted from a sensor. This signal corresponds in turn to the intensity of the temperature at the tissue site. Therefore a voltage level of 2 would indicate that the tissue was hotter than when the voltage level was 1. In this example, a user may monitor the voltage level and, if it exceeded a certain value, may turn off or adjust a power source.

An indicator, such as an LED light, may be permanently or removably incorporated into suction tool 10. The indicator may receive a signal from one or more sensors indicating that the tissue had reached an appropriate temperature, for example. In response, the indicator may turn on, change color, grow brighter or change in any suitable manner to indicate that the flow of power from a power source should be modified or halted. The indicator may be located anywhere that would be visible to the user.

Alternatively, an output device may be an audio device that indicates to the user the status of a medical procedure. Such an audio device may be, for example, a speaker that broadcasts a sound (for example, a beep) that increases in intensity, frequency or tone as a characteristic of the procedure has changed, for example, the temperature measured by a sensor. The user may adjust, for example, turn down or turn off a power source when the sound emitted reaches a given volume or level. In another embodiment, the audio device may also give an audible signal (such as the message "turn off power source") when the temperature, for example, sensed by one or more sensors reaches a certain level. Such an audio device may be incorporated in suction tool 10 or the audio device may be a separate device coupled to suction tool 10.

Suction tool 10 may be permanently or removably attached to a source of energy such as electrical, radiofrequency (RF), laser, thermal, microwave or ultrasound or any other appropriate type of energy that may be used during a medical procedure including the use of suction tool 10. The energy source may be powered by AC current, DC current or it may be battery powered either by a disposable or re-chargeable battery. The energy source may incorporate a controller or any suitable processor. For example, the processor may gather and/or process sensed information from one or more sensors. The controller may store and/or process such information before, during and/or after a medical procedure. For example, the patient's tissue temperature may be sensed, stored and processed prior to and during an ablation procedure.

The information stored and/or processed may be used to adjust power levels and delivery times. An energy source may incorporate one or more switches or be coupled to one or more switches of suction tool 10 to facilitate regulation of the various system components by the surgeon. An energy source may be coupled to an output device or an output device may be incorporated into the energy source. The energy source may incorporate a cardiac stimulator and/or cardiac monitor. For example, electrodes used to stimulate or monitor the heart may be incorporated into suction tool 10. An energy source coupled to suction tool 10 may comprise a surgeon-controlled switch for cardiac stimulation or monitoring. A visual and/or audible signal used to alert a surgeon to the completion or resumption of ablation, suction, sensing, monitoring, stimulation and/or delivery of irrigation fluid, drugs and/or cells may be incorporated into an energy source and/or suction tool 10. For example, a beeping tone or flashing light that increases in frequency as the ablation period ends or begins may be used.

Delivery of suction, energy, cells, and/or fluids may be slaved to one or more sensors of suction tool 10. For example, the delivery of energy may be designed to automatically stop if a sensor measures a predetermined sensor value, e.g., a particular temperature value. In one embodiment of the invention, if a sensor of the present invention indicates that tissue has reached a particular temperature, the delivery of energy is stopped automatically, thereby preventing charring of the tissue.

One or more of a variety of diagnostic agents, therapeutic agents, pharmacological agents and/or drugs may be delivered or administered to the patient during a medical procedure performed according to the present invention, prior to a medical procedure performed according to the present invention, intermittently during a medical procedure performed according to the present invention, continuously during a medical procedure performed according to the present invention and/or following a medical procedure performed according to the present invention. For example, one or more of a variety of pharmacological agents or drugs, as discussed below, may be delivered before, during or after an ablation procedure, as discussed earlier.

Drugs, drug formulations or compositions suitable for administration to a patient may include a pharmaceutically acceptable carrier or solution in an appropriate dosage. There are a number of pharmaceutically acceptable carriers that may be used for delivery of various drugs, for example, via direct injection, oral delivery, suppository delivery, transdermal delivery, epicardial delivery and/or inhalation delivery. Pharmaceutically acceptable carriers include a number of solutions, preferably sterile, for example, water, saline, Ringer's solution and/or sugar solutions such as dextrose in water or saline. Other possible carriers that may be used include sodium citrate, citric acid, amino acids, lactate, mannitol, maltose, glycerol, sucrose, ammonium chloride, sodium chloride, potassium chloride, calcium chloride, sodium lactate, and/or sodium bicarbonate. Carrier solutions may or may not be buffered.

Drug formulations or compositions may include antioxidants or preservatives such as ascorbic acid. They may also be in a pharmaceutically acceptable form for parenteral administration, for example to the cardiovascular system, or directly to the heart, such as intracoronary infusion or injection. Drug formulations or compositions may comprise agents that provide a synergistic effect when administered together. A synergistic effect between two or more drugs or agents may reduce the amount that normally is required for therapeutic delivery of an individual drug or agent. Two or more drugs may be administered, for example, sequentially or simultaneously. Drugs may be administered via one or more bolus injections and/or infusions or combinations thereof. The injections and/or infusions may be continuous or intermittent. Drugs may be administered, for example, systemically or locally, for example, to the heart, to a coronary artery and/or vein, to a pulmonary artery and/or vein, to the right atrium and/or ventricle, to the left atrium and/or ventricle, to the aorta, to the AV node, to the SA node, to a nerve and/or to the coronary sinus. Drugs may be administered or delivered via intravenous, intracoronary and/or intraventricular administration in a suitable carrier. Examples of arteries that may be used to deliver drugs to the AV node include the AV node artery, the right coronary artery, the right descending coronary artery, the left coronary artery, the left anterior descending coronary artery and Kugel's artery. Drugs may be delivered systemically, for example, via oral, transdermal, intranasal, suppository or inhalation methods. Drugs also may be delivered via a pill, a spray, a cream, an ointment or a medicament formulation.

In one embodiment of the present invention, suction tool 10 may incorporate a delivery device for delivering one or more diagnostic agents, therapeutic agents, pharmacological agents and/or drugs. Alternatively, a delivery device may be advanced through working lumen 20 and out port 46 of suction tool 10. For example, a delivery device such as a needle or catheter may be inserted into working lumen 20. A delivery catheter may include an expandable member, e.g., a low-pressure balloon, and a shaft having a distal portion, wherein the expandable member is disposed along the distal portion. A delivery catheter may comprise one or more lumens. A delivery catheter or needle may be advanced through working lumen 20 and out port 46 and into tissue and/or a blood vessel, e.g., an artery such as a femoral, radial, subclavian or coronary artery. Suction tool 10 can be guided into a desired position using various guidance techniques, e.g., flouroscopic guidance and/or a guiding catheter or guide wire placed through working lumen 20 or a guide lumen (not shown). Drugs may be delivered with suction tool 10 via iontophoresis. In general, the delivery of ionized drugs may be enhanced via a small current applied across two electrodes, for example, one or more electrodes located on suction pad 30. Positive ions may be introduced into the tissues from the positive pole, or negative ions from the negative pole. The use of iontophoresis may markedly facilitate the transport of certain ionized drug molecules. For example, lidocaine hydrochloride may be applied to the heart using iontophoresis. A positive electrode could be located on suction pad 30 while the negative electrode could contact the heart or other body part at some desired distance point to complete the circuit. One or more of the iontophoresis electrodes may also be used as nerve stimulation electrodes or as cardiac stimulation electrodes.

Diagnostic or therapeutic agents, such as one or more radioactive materials and/or biological agents such as, for example, an anticoagulant agent, an antithrombotic agent, a clotting agent, a platelet agent, an anti-inflammatory agent, an antibody, an antigen, an immunoglobulin, a defense agent, an enzyme, a hormone, a growth factor, a neurotransmitter, a cytokine, a blood agent, a regulatory agent, a transport agent, a fibrous agent, a protein, a peptide, a proteoglycan, a toxin, an antibiotic agent, an antibacterial agent, an antimicrobial agent, a bacterial agent or component, hyaluronic acid, a polysaccharide, a carbohydrate, a fatty acid, a catalyst, a drug, a vitamin, a DNA segment, a RNA segment, a nucleic acid, a lectin, an antiviral agent, a viral agent or component, a genetic agent, a ligand and a dye (which acts as a biological ligand) may be delivered. Biological agents may be found in nature (naturally occurring) or may be chemically synthesized. Cells and/or cell components, e.g., mammalian cells, may be delivered. Blood and/or blood components, e.g., platelet rich plasma or autologous platelet gel, may be delivered. One or more tissue sealants, glues or adhesives may be delivered.

A delivery device may be incorporated into suction tool 10, thereby delivering biological agents at or adjacent the suction tool site, or the delivery device may be placed or used at a location differing from the location of suction tool 10. For example, a delivery device may be placed in contact with the inside surface of a patient's heart while suction tool 10 is placed or used on the outside surface of the patient's heart.

The delivery device may be slaved to an output device. For example, a delivery device may be designed to automatically stop or start the delivery of drugs or agents during the placement of a lead. The delivery device may be slaved to a robotic system or a robotic system may be slaved to the delivery device.

The delivery device may comprise a surgeon-controlled switch. For example, a switch may be incorporated in or on the delivery device, suction tool 10, or any other location easily and quickly accessed by the surgeon. The switch may be, for example, a hand switch, a foot switch, or a voice-activated switch comprising voice-recognition technologies.

The delivery device may include a visual and/or audible signal used to alert a surgeon to any change in the delivery of agents. For example, a beeping tone or flashing light that increases in frequency as the rate of drug delivery increases may be used to alert the surgeon.

The two divisions of the autonomic nervous system that regulate the heart have opposite functions. First, the adrenergic or sympathetic nervous system increases heart rate by releasing epinephrine and norepinephrine. Second, the parasympathetic system also known as the cholinergic nervous system or the vagal nervous system decreases heart rate by releasing acetylcholine. Catecholamines such as norepinephrine (also called noradrenaline) and epinephrine (also called adrenaline) are agonists for beta-adrenergic receptors. An agonist is a stimulant biomblecule or agent that binds to a receptor.

Beta-adrenergic receptor blocking agents compete with beta-adrenergic receptor stimulating agents for available beta-receptor sites. When access to beta-receptor sites are blocked by receptor blocking agents, also known as beta-adrenergic blockade, the chronotropic or heart rate, inotropic or contractility, and vasodilator responses to receptor stimulating agents are decreased proportionately. Therefore, beta-adrenergic receptor blocking agents are agents that are capable of blocking beta-adrenergic receptor sites. Since beta-adrenergic receptors are concerned with contractility and heart rate, stimulation of beta-adrenergic receptors, in general, increases heart rate, the contractility of the heart and the rate of conduction of electrical impulses through the AV node and the conduction system.

Drugs, drug formulations and/or drug compositions that may be used according to this invention may include anynaturally occurring or chemically synthesized (synthetic analogues) beta-adrenergic receptor blocking agents. Beta-adrenergic receptor blocking agents or β-adrenergic blocking agents are also known as beta-blockers or β-blockers and as class II antiarrhythmics.

The term "beta-blocker" appearing herein may refer to one or more agents that antagonize the effects of beta-stimulating catecholamines by blocking the catecholamines from binding to the beta-receptors. Examples of beta-blockers include, but are not limited to, acebutolol, alprenolol, atenolol, betantolol, betaxolol, bevantolol, bisoprolol, carterolol, celiprolol, chlorthalidone, esmolol, labetalol, metoprolol, nadolol, penbutolol, pindolol, propranolol, oxprenolol, sotalol, teratolo, timolol and combinations, mixtures and/or salts thereof. The effects of administered beta-blockers may be reversed by administration of beta-receptor agonists, e.g., dobutamine or isoproterenol.

The parasympathetic or cholinergic system participates in control of heart rate via the sinoatrial (SA) node, where it reduces heart rate. Other cholinergic effects include inhibition of the AV node and an inhibitory effect on contractile force. The cholinergic system acts through the vagal nerve to release acetylcholine, which, in turn, stimulates cholinergic receptors. Cholinergic receptors are also known as muscarinic receptors. Stimulation of the cholinergic receptors decreases the formation of cAMP. Stimulation of cholinergic receptors generally has an opposite effect on heart rate compared to stimulation of beta-adrenergic receptors. For example, beta-adrenergic stimulation increases heart rate, whereas cholinergic stimulation decreases it. When vagal tone is high and adrenergic tone is low, there is a marked slowing of the heart (sinus bradycardia). Acetylcholine effectively reduces the amplitude, rate of increase and duration of the SA node action potential. During vagal nerve stimulation, the SA node does not arrest. Rather, pacemaker function may shift to cells that fire at a slower rate. In addition, acetylcholine may help open certain potassium channels thereby creating an outward flow of potassium ions and hyperpolarization. Acetylcholine also slows conduction through the AV node.

Drugs, drug formulations and/or drug compositions that may be used according to this invention may include any naturally occurring or chemically synthesized (synthetic analogues) cholinergic agent. The term "cholinergic agent" appearing herein may refer to one or more cholinergic receptor modulators or agonists. Examples of cholinergic agents include, but are not limited to, acetylcholine, carbachol (carbamyl choline chloride), bethanechol, methacholine, arecoline, norarecoline and combinations, mixtures and/or salts thereof.

Drugs, drug formulations and/or drug compositions that may be used according to this invention may include any naturally occurring or chemically synthesized cholinesterase inhibitor. The term "cholinesterase inhibitor" appearing herein may refer to one or more agents that prolong the action of acetylcholine by inhibiting its destruction or hydrolysis by cholinesterase. Cholinesterase inhibitors are also known as acetylcholinesterase inhibitors. Examples of cholinesterase inhibitors include, but are not limited to, edrophonium, neostigmine, neostigmine methylsulfate, pyridostigmine, tacrine and combinations, mixtures and/or salts thereof.

There are ion-selective channels within certain cell membranes. These ion selective channels include calcium channels, sodium channels and/or potassium channels. Therefore, other drugs, drug formulations and/or drug compositions that may be used according to this invention may include any naturally occurring or chemically synthesized calcium channel blocker. Calcium channel blockers inhibit the inward flux of calcium ions across cell membranes of arterial smooth muscle cells and myocardial cells. Therefore, the term "calcium channel blocker" appearing herein may refer to one or more agents that inhibit or block the flow of calcium ions across a cell membrane. The calcium channel is generally concerned with the triggering of the contractile cycle. Calcium channel blockers are also known as calcium ion influx inhibitors, slow channel blockers, calcium ion antagonists, calcium channel antagonist drugs and as class IV antiarrhythmics. A commonly used calcium channel blocker is verapamil.

Administration of a calcium channel blocker, e.g., verapamil, generally prolongs the effective refractory period within the AV node and slows AV conduction in a rate-related manner, since the electrical activity through the AV node depends significantly upon the influx of calcium ions through the slow channel. A calcium channel blocker has the ability to slow a patient's heart rate, as well as produce AV block. Examples of calcium channel blockers include, but are not limited to, amiloride, amlodipine, bepridil, diltiazem, felodipine, isradipine, mibefradil, nicardipine, nifedipine (dihydropyridines), nickel, nimodinpine, nisoldipine, nitric oxide (NO), norverapamil and verapamil and combinations, mixtures and/or salts thereof. Verapamil and diltiazem are very effective at inhibiting the AV node, whereas drugs of the nifedipine family have a lesser inhibitory effect on the AV node. Nitric oxide (NO) indirectly promotes calcium channel closure. NO may be used to inhibit contraction. NO may also be used to inhibit sympathetic outflow, lessen the release of norepinephrine, cause vasodilation, decrease heart rate and decrease contractility. In the SA node, cholinergic stimulation leads to formation of NO.

Other drugs, drug formulations and/or drug compositions that may be used according to this invention may include any naturally occurring or chemically synthesized sodium channel blocker. Sodium channel blockers are also known as sodium channel inhibitors, sodium channel blocking agents, rapid channel blockers or rapid channel inhibitors. Antiarrhythmic agents that inhibit or block the sodium channel are known as class I antiarrhythmics, examples include, but are not limited to, quinidine and quinidine-like agents, lidocaine and lidocaine-like agents, tetrodotoxin, encainide, flecainide and combinations, mixtures and/or salts thereof. Therefore, the term "sodium channel blocker" appearing herein may refer to one or more agents that inhibit or block the flow of sodium ions across a cell membrane or remove the potential difference across a cell membrane. For example, the sodium channel may also be totally inhibited by increasing the extracellular potassium levels to depolarizing hyperkalemic values, which remove the potential difference across the cell membrane. The result is inhibition of cardiac contraction with cardiac arrest (cardioplegia). The opening of the sodium channel (influx of sodium) is for swift conduction of the electrical impulse throughout the heart.

Other drugs, drug formulations and/or drug compositions that may be used according to this invention may include any naturally occurring or chemically synthesized potassium channel agent. The term "potassium channel agent" appearing herein may refer to one or more agents that impact the flow of potassium ions across the cell membrane. There are two major types of potassium channels. The first type of channel is voltage-gated and the second type is ligand-gated. Acetylcholine-activated potassium channels, which are ligand-gated channels, open in response to vagal stimulation and the release of acetylcholine. Opening of the potassium channel causes hyperpolarization, which decreases the rate at which the activation threshold is reached. Adenosine is one example of a potassium channel opener. Adenosine slows conduction through the AV node. Adenosine, a breakdown product of adenosine triphosphate, inhibits the AV node and atria. In atrial tissue, adenosine causes the shortening of the action potential duration and causes hyperpolarization. In the AV node, adenosine has similar effects and also decreases the action potential amplitude and the rate of increase of the action potential. Adenosine is also a direct vasodilator by its actions on the adenosine receptor on vascular smooth muscle cells. In addition, adenosine acts as a negative neuromodulator, thereby inhibiting release of norepinephrine. Class III antiarrhythmic agents also known as potassium channel inhibitors lengthen the action potential duration and refractoriness by blocking the outward potassium channel to prolong the action potential. Amiodarone and d-sotalol are both examples of class III antiarrhythmic agents.

Potassium is the most common component in cardioplegic solutions. High extracellular potassium levels reduce the membrane resting potential. Opening of the sodium channel, which normally allows rapid sodium influx during the upstroke of the action potential, is therefore inactivated because of a reduction in the membrane resting potential.

Drugs, drug formulations and/or drug compositions that may be used according to this invention may comprise one or more of any naturally occurring or chemically synthesized beta-blocker, cholinergic agent, cholinesterase inhibitor, calcium channel blocker, sodium channel blocker, potassium channel agent, adenosine, adenosine receptor agonist, adenosine deaminase inhibitor, dipyridamole, monoamine oxidase inhibitor, digoxin, digitalis, lignocaine, bradykinin agents, serotoninergic agonist, antiarrythmic agents, cardiac glycosides, local anesthetics and combinations or mixtures thereof. Digitalis and digoxin both inhibit the sodium pump. Digitalis is a natural inotrope derived from plant material, while digoxin is a synthesized inotrope. Dipyridamole inhibits adenosine deaminase, which breaks down adenosine. Drugs, drug formulations and/or drug compositions capable of reversibly suppressing autonomous electrical conduction at the SA and/or AV node, while still allowing the heart to be electrically paced to maintain cardiac output may be used according to this invention.

Beta-adrenergic stimulation or administration of calcium solutions may be used to reverse the effects of a calcium channel blocker such as verapamil. Agents that promote heart rate and/or contraction may be used in the present invention. For example, dopamine, a natural catecholamine, is known to increase contractility. Positive inotropes are agents that specifically increase the force of contraction of the heart. Glucagon, a naturally occurring hormone, is known to increase heart rate and contractility. Glucagon may be used to reverse the effects of a beta-blocker since its effects bypass the beta receptor. Forskolin is known to increase heart rate and contractility. As mentioned earlier, epinephrine and norepinephrine naturally increase heart rate and contractility. Thyroid hormone, phosphodiesterase inhibitors and prostacyclin, a prostaglandin, are also known to increase heart rate and contractility. In addition, methylxanthines are known to prevent adenosine from interacting with its cell receptors. Suction tool 10 can be modified to incorporate one or more fluid lumens and/or conduits for providing one or more fluids, e.g., irrigation fluid to an ablation site.

Tissues and organs of a patient, such as the heart, lung, liver, stomach, intestine, spleen, brain, spine, bone, muscle, and tumor, may be treated using the present invention.

All patents and publications referenced herein are hereby incorporated by reference in their entireties.

It will be understood that certain of the above-described structures, functions and operations of the above-described preferred embodiments are not necessary to practice the present invention and are included in the description simply for completeness of an exemplary embodiment or embodiments.

In addition, it will be understood that specifically described structures, functions and operations set forth in the above-referenced patents can be practiced in conjunction with the present invention, but they are not essential to its practice. It is therefore to be understood, that within the scope of the appended claims, the invention may be practiced otherwise than as specifically described without actually departing from the spirit and scope of the present invention.

What is claimed is:

1. A suction tool for accessing the epicardium of the heart through an incision through the pericardium and into the pericardial space to ablate myocardium tissue comprising:

a suction tool body extending between a suction tool body proximal end and a suction tool body distal end; and an elongated suction pad extending between a suction pad proximal end and a suction pad distal end, the suction pad proximal end attached to the suction tool body distal end, the suction pad shaped to have a suction cavity adapted to be applied against tissue, the suction cavity defined by an elongated, substantially concave suction cavity wall bounded by a suction cavity rim, a plurality of suction ports extending through the suction cavity wall into the suction cavity, the suction pad distal end shaped with a leader to fit through a pericardial incision and a tissue dilator to be inserted through the pericardial incision to facilitate advancement of the suction pad into the pericardial space, the suction pad comprising one or more ablation electrodes, the suction tool body further comprising:
a suction lumen extending from a proximal suction fitting adapted to be coupled to a vacuum source and to the plurality of suction ports through which suction is applied to the pericardium to draw a pericardial bleb of the pericardium into the suction cavity when the suction cavity wall is applied against the pericardium and through which suction is applied to the epicardium to draw an myocardial bleb of the myocardium into the suction cavity when the suction pad is inserted through an incision of the pericardium into the suction cavity wall and applied against the epicardium; and a working lumen extending between a working lumen proximal end opening and an working lumen distal end opening into the suction cavity, the working lumen adapted to receive an ablation tool having one or more electrodes for ablating for ablating myocardium tissue.

2. The suction tool of claim 1, wherein the suction tool further comprises:
a light conducting pipe extending between a light conducting pipe proximal end adapted to be coupled to a light source outside the patient's body and a light emitting distal end at the suction pad located to provide illumination about the suction pad; and
an image conducting pipe extending between an image conducting pipe proximal end adapted to be coupled to an image capturing camera and image display outside the patient's body and an image conducting pipe at the suction pad to image the pericardium or epicardium adjacent the suction pad.

3. The suction tool of claim 1, wherein the suction tool further comprises:
a light conducting pipe extending between a light conducting pipe proximal end adapted to be coupled to a light source outside the patient's body and a light emitting distal end at the suction cavity wall located to provide illumination about the suction cavity wall; and
an image conducting pipe extending between an image conducting pipe proximal end adapted to be coupled to an image capturing camera and image display outside the patient's body and an image conducting pipe at the suction cavity wall to image the pericardium or epicardium adjacent the suction cavity wall.

4. The suction tool of claim 1, wherein the suction tool further comprises:
a light conducting pipe extending between a light conducting pipe proximal end adapted to be coupled to a light source outside the patient's body and a light emitting distal end adjacent the tissue dilator to provide illumination about the suction pad distal end; and
an image conducting pipe extending between an image conducting pipe proximal end adapted to be coupled to an image capturing camera and image display outside the patient's body and an image conducting pipe adjacent the tissue dilator to image the pericardium or epicardium adjacent the suction pad distal end.

5. The suction tool of claim 1, wherein the suction tool further comprises:
means for providing illumination of the pericardium or epicardium adjacent the suction pad; and
means for providing an image of the illuminated pericardium or epicardium adjacent the suction pad.

6. The suction tool of claim 1, wherein the suction tool further comprises:
means for providing illumination of the pericardium or epicardium adjacent the suction cavity wall; and
means for providing an image of the illuminated pericardium or epicardium adjacent the suction cavity wall.

7. The suction tool of claim 1, wherein the suction tool further comprises:
means for providing illumination of the pericardium or epicardium adjacent the tissue dilator to provide illumination about the suction pad distal end; and
means for providing an image of the illuminated pericardium or epicardium adjacent the tissue dilator to image tissue adjacent the suction pad distal end.

8. A system for accessing the epicardium of the heart through an incision through the pericardium and into the pericardial space to implant cells into the myocardium comprising:
a suction tool comprising:
a suction tool body extending between a suction tool body proximal end and a suction tool body distal end; and
an elongated suction pad extending between a suction pad proximal end and a suction pad distal end, the suction pad proximal end attached to the suction tool body distal end, the suction pad shaped to have a suction cavity adapted to be applied against tissue, the suction cavity defined by an elongated, substantially concave suction cavity wall bounded by a suction cavity rim, a plurality of suction ports extending through the suction cavity wall into the suction cavity, the suction pad distal end shaped to form a tissue dilator to be inserted through an incision made through the pericardium to facilitate advancement of the suction pad into the pericardial space,
the suction tool body further comprising a suction lumen extending from a proximal suction fitting adapted to be coupled to a vacuum source and to the plurality of suction ports suction through which suction is applied to the pericardium to draw a pericardial bleb of the pericardium into the suction cavity when the suction cavity wall is applied against the pericardium and through which suction is applied to the epicardium to draw an myocardial bleb of the myocardium into the suction cavity when the suction pad is inserted through an incision of the pericardium into the suction cavity wall and applied against the epicardium, and a working lumen extending between a working lumen proximal end opening and an working lumen distal end opening into the, suction cavity; and
a cutting instrument having a cutting element adapted to be inserted through the working lumen for cutting into the pericardial bleb to form a pericardial incision through which the suction pad can be inserted into the pericardial space,
whereby a catheter for inserting cells into tissue can be inserted through the working lumen to implant cells in the myocardium.

9. The system of claim 8, wherein the suction tool further comprises:
a light conducting pipe extending between a light conducting pipe proximal end adapted to be coupled to a light source outside the patient's body and a light emitting distal end at the suction pad located to provide illumination about the suction pad; and
an image conducting pipe extending between an image conducting pipe proximal end adapted to be coupled to an image capturing camera and image display outside the patient's body and an image conducting pipe at the suction pad to image the pericardium or epicardium adjacent the suction pad.

10. The system of claim 8, wherein the suction tool further comprises:
a light conducting pipe extending between a light conducting pipe proximal end adapted to be coupled to a light source outside the patient's body and a light emitting distal end at the suction cavity wall located to provide illumination about the suction cavity wall; and
an image conducting pipe extending between an image conducting pipe proximal end adapted to be coupled to an image capturing camera and image display outside the patient's body and an image conducting pipe at the suction cavity wall to image the pericardium or epicardium adjacent the suction cavity wall.

11. The system of claim 8, wherein the suction tool further comprises:
a light conducting pipe extending between a light conducting pipe proximal end adapted to be coupled to a light source outside the patient's body and a light emitting distal end adjacent the tissue dilator to provide illumination about the suction pad distal end; and
an image conducting pipe extending between an image conducting pipe proximal end adapted to be coupled to an image capturing camera and image display outside the patient's body and an image conducting pipe adjacent the tissue dilator to image the pericardium or epicardium adjacent the suction pad distal end.

12. The system of claim 8, wherein the suction tool further comprises:
means for providing illumination of the pericardium or epicardium adjacent the suction pad; and
means for providing an image of the illuminated pericardium or epicardium adjacent the suction pad.

13. The system of claim 8, wherein the suction tool further comprises:
means for providing illumination of the pericardium or epicardium adjacent the suction cavity wall; and
means for providing an image of the illuminated pericardium or epicardium adjacent the suction cavity wall.

14. The system of claim 8, wherein the suction tool further comprises:
means for providing illumination of the pericardium or epicardium adjacent the tissue dilator to provide illumination about the suction pad distal end; and
means for providing an image of the illuminated pericardium or epicardium adjacent the tissue dilator to image tissue adjacent the suction pad distal end.

15. A method of ablation comprising:
inserting a suction tool body extending between a suction tool body proximal end and a suction tool body distal end through a pathway in the body to dispose a suction pad of the suction tool in proximity to the epicardium, the suction pad extending between a suction pad proximal end and a suction pad distal end, the suction pad proximal end attached to the suction tool body distal end, the suction pad shaped to have a suction cavity adapted to be applied against tissue, the suction cavity defined by an elongated, substantially concave suction cavity wall bounded by a suction cavity rim, a plurality of suction ports extending through the suction cavity wall to a suction lumen extending through the suction tool body to the suction tool body proximal end, and a working lumen extending from the suction tool proximal end into the suction cavity;
forming a pericardial incision;
advancing the suction pad through the pericardial incision to dispose the suction cavity against the epicardium;
applying suction through the suction lumen and the suction ports to the epicardium to draw an myocardial bleb of the myocardium into the suction cavity;
advancing an ablation tool through the working lumen; and
ablating the myocardial bleb.

16. The method of claim 15, wherein the step of advancing the suction pad through the pericardial incision to dispose the suction cavity against the epicardium comprises; illuminating the pericardial space and imaging the illuminated pericardial space to facilitate the application of the suction cavity against the epicardium.

17. The method of claim 15, wherein:
the suction tool inserted in the inserting step comprises a light conducting pipe extending between a light conducting pipe proximal end adapted to be coupled to a light source outside the patient's body and a light emitting distal end at the suction pad located to provide illumination about the suction pad, and an image conducting pipe extending between an image conducting pipe proximal end adapted to be coupled to an image capturing camera and image display outside the patient's body and an image conducting pipe at the suction pad to image the pericardium or epicardium adjacent the suction pad; and
the step of advancing the suction pad through the pericardial incision to dispose the suction cavity against the epicardium comprises illuminating the pericardial space through the light conducting pipe and imaging the illuminated pericardial space through the image conducting pipe to facilitate the application of the suction cavity against the epicardium.

18. The method of claim 15, further comprising:
the step of advancing a cardiac lead having a distal fixation mechanism through the working lumen;
restraining the distal fixation mechanism within a lead installation tool adjacent a tool distal end;
advancing the lead installation tool through the working lumen;
forming a proximal epicardial perforation of the myocardial bleb with the tool distal end;
advancing the tool distal end through the myocardial bleb; and
forming a distal epicardial perforation of the myocardial bleb with the tool distal end; and
the step of fixing the distal fixation mechanism to the myocardial bleb comprises:
releasing the distal fixation mechanism from the tool distal end to bear against the epicardium;
releasing the suction of the epicardium; and
withdrawing the lead installation tool and the suction tool from the cardiac lead.

19. The method of claim 17, wherein the cardiac lead comprises a lead body bearing a pace/sense electrode and a fixation helix, and the step of fixing the distal fixation mechanism to the myocardial bleb comprises:
rotating the lead body to screw the fixation helix through the epicardium and into the myocardium;
releasing the suction of the epicardium; and
withdrawing the suction tool from the cardiac lead.

* * * * *